United States Patent
Zhong et al.

(10) Patent No.: US 9,006,337 B2
(45) Date of Patent: Apr. 14, 2015

(54) METHOD FOR MAKING A POLYMER, A POLYMER ARTICLE, A BIODEVICE, AND CYCLIC CARBONATE

(75) Inventors: Zhiyuan Zhong, Suzhou (CN); Fenghua Meng, Suzhou (CN); Rong Wang, Suzhou (CN); Jan Feijen, Hengelo (NL)

(73) Assignee: Ssens B.V., Enschede (NL)

( * ) Notice: Subject to any disclaimer, the term of this patent is extended or adjusted under 35 U.S.C. 154(b) by 0 days.

(21) Appl. No.: 14/130,824

(22) PCT Filed: Jul. 4, 2011

(86) PCT No.: PCT/EP2011/061256
§ 371 (c)(1),
(2), (4) Date: Apr. 29, 2014

(87) PCT Pub. No.: WO2013/004296
PCT Pub. Date: Jan. 10, 2013

(65) Prior Publication Data
US 2014/0249268 A1    Sep. 4, 2014

(51) Int. Cl.
| | |
|---|---|
| C08G 63/60 | (2006.01) |
| C08G 64/30 | (2006.01) |
| C07D 319/06 | (2006.01) |
| C08G 64/02 | (2006.01) |
| C08G 63/64 | (2006.01) |
| C08G 63/688 | (2006.01) |
| A61L 31/10 | (2006.01) |
| A61L 31/14 | (2006.01) |
| C08G 67/00 | (2006.01) |

(52) U.S. Cl.
CPC .............. *C08G 64/30* (2013.01); *C07D 319/06* (2013.01); *C08G 64/025* (2013.01); *C08G 63/64* (2013.01); *C08G 63/688* (2013.01); *C08G 64/0291* (2013.01); *A61L 31/10* (2013.01); *A61L 31/148* (2013.01)

(58) Field of Classification Search
USPC .......................................... 524/599; 528/354
See application file for complete search history.

(56) References Cited

U.S. PATENT DOCUMENTS

2010/0280219 A1    11/2010    Cooley et al.

FOREIGN PATENT DOCUMENTS

| | | |
|---|---|---|
| JP | 2001-131170 A | 5/2001 |
| WO | WO 2011/009478 A1 | 1/2011 |

OTHER PUBLICATIONS

Synthesis of Functionalized Cyclic Carbonate Monomers Using a Versatile Pentafluoro Phenylcarbonate Intermediate; Daniel P. Sanders, et al; .Polym. Chem., 2014, 5, 327.*
International Search Report dated Mar. 22, 2012 with Written Opinion for International Application No. PCT/EP2011/061256.
International Preliminary Report on Patentability dated Jan. 7, 2014, for International Application No. PCT/EP2011/061256.

* cited by examiner

*Primary Examiner* — Terressa Boykin
(74) *Attorney, Agent, or Firm* — Cook Alex Ltd.

(57) ABSTRACT

The present invention relates to a method for making a polymer wherein during ring opening polymerisation is incorporated into the polymer chain at least one cyclic (alkyl) carbonate monomer having the formula (1) wherein Y is optional and represents the residue of a sulfhydryl reacted group, X represents a functional group reactive with a sulfhydryl group, L=—[CH2]n with n=0-10, or L=—[CH2]p-S—S—[CH2]q with p and q are 0-5 or L=-[PEG]- with PEG is a group that comprises a —[CH2CH2O]m-group with m=1-200, and R2 is hydrogen, methyl or ethyl. Optionally a cyclic (alkyl) acryloyl carbonate, or other additional monomer A may be used as comonomer. The polymer may be formed into a polymer article, such as a polymer film, such as a coating and modified and/or cross linked, to a polymer or polymer article obtainable, and to a biodevice, their use, and to the cyclic (alkyl)carbonates.

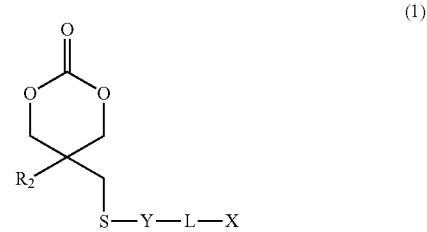

(1)

20 Claims, 7 Drawing Sheets

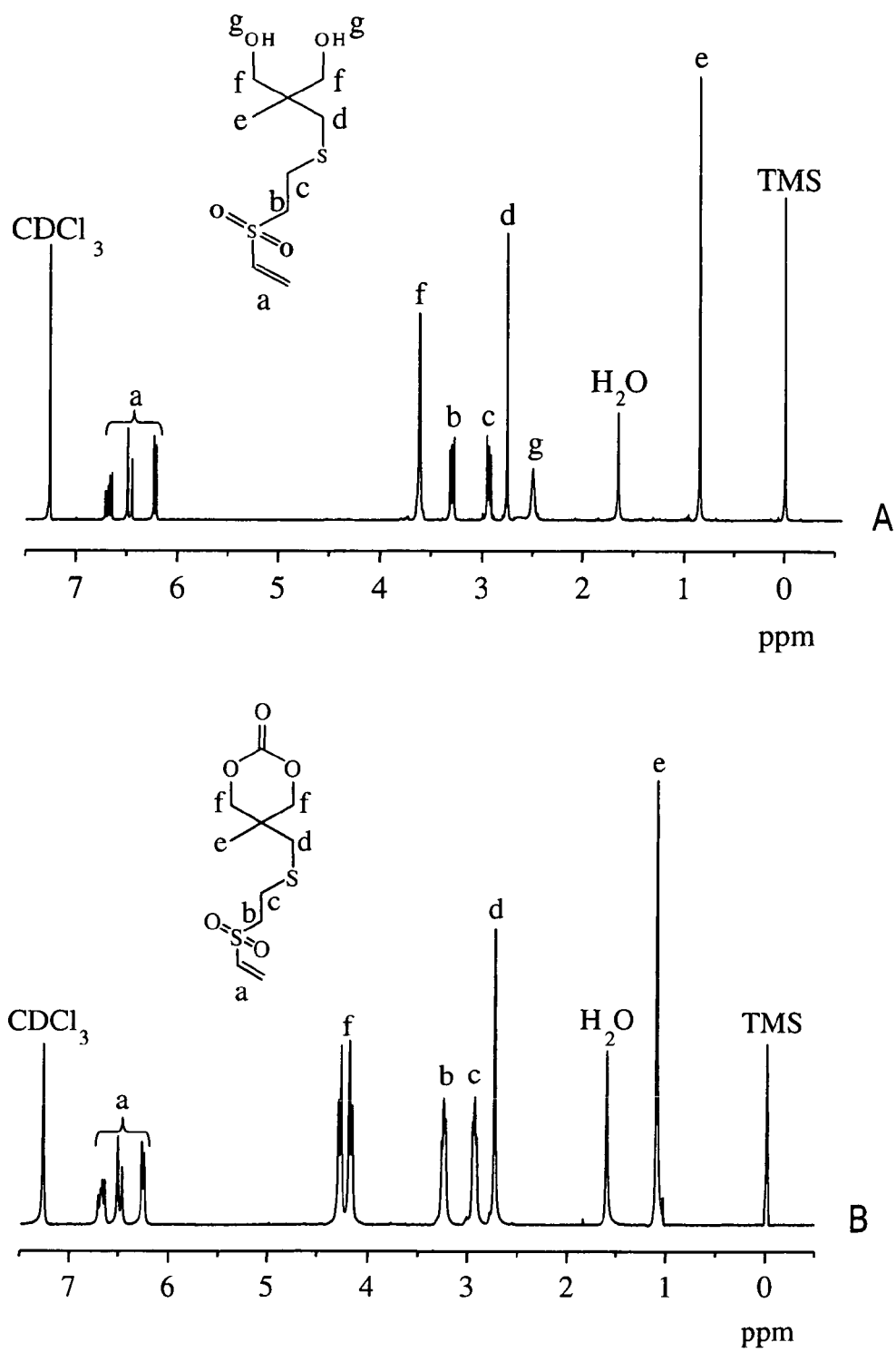
Fig.1 1H NMR spectra (400 MHz, CDCl3) of vinyl sulfone-diol (A) and VSC (B).

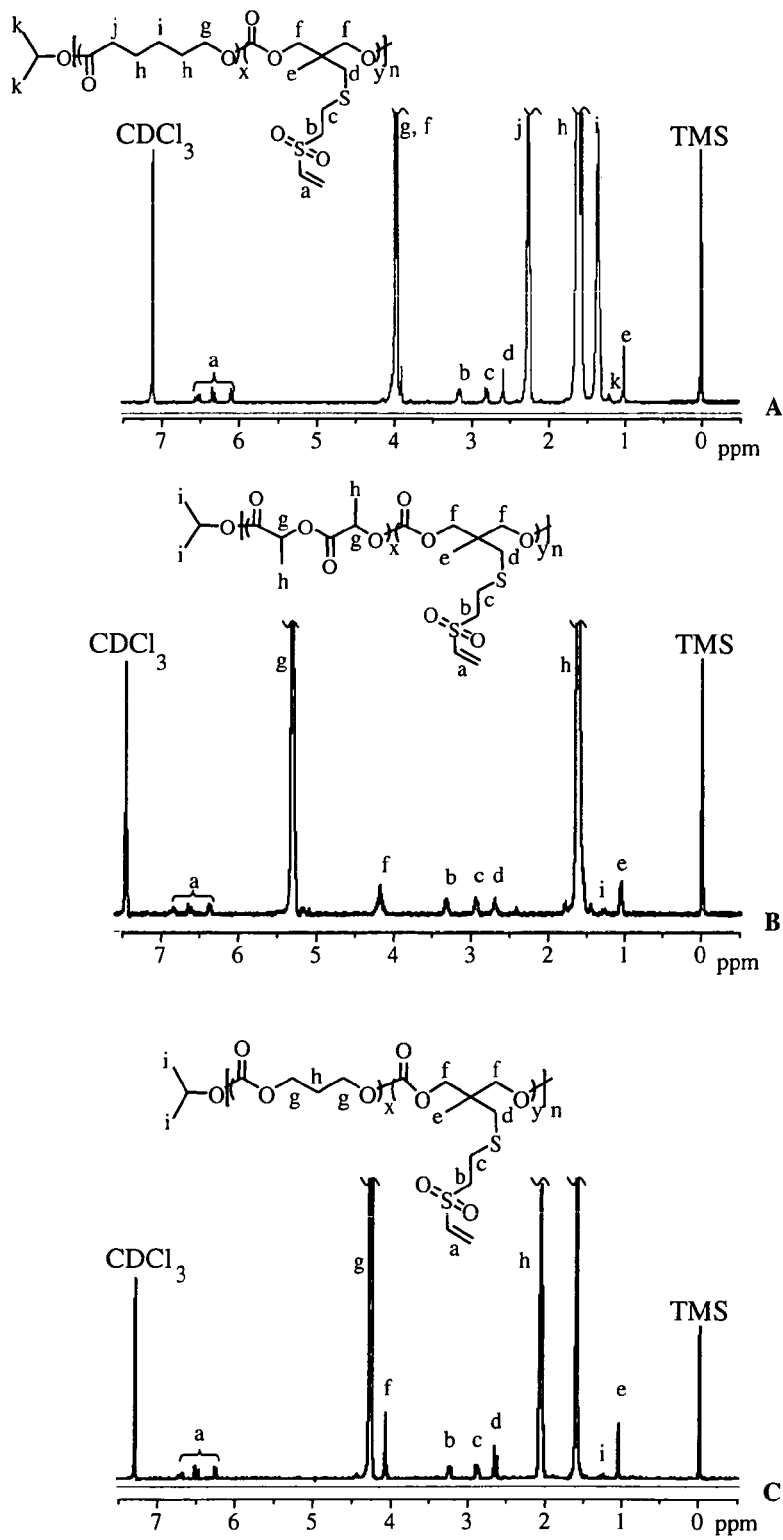
Fig.2 1H NMR spectra (400 MHz, CDCl3) of VS-functionalized biodegradable polymers. (A) P(CL-co-VSC); (B) P(LA-co-VSC); (C) P(TMC-co-VSC).

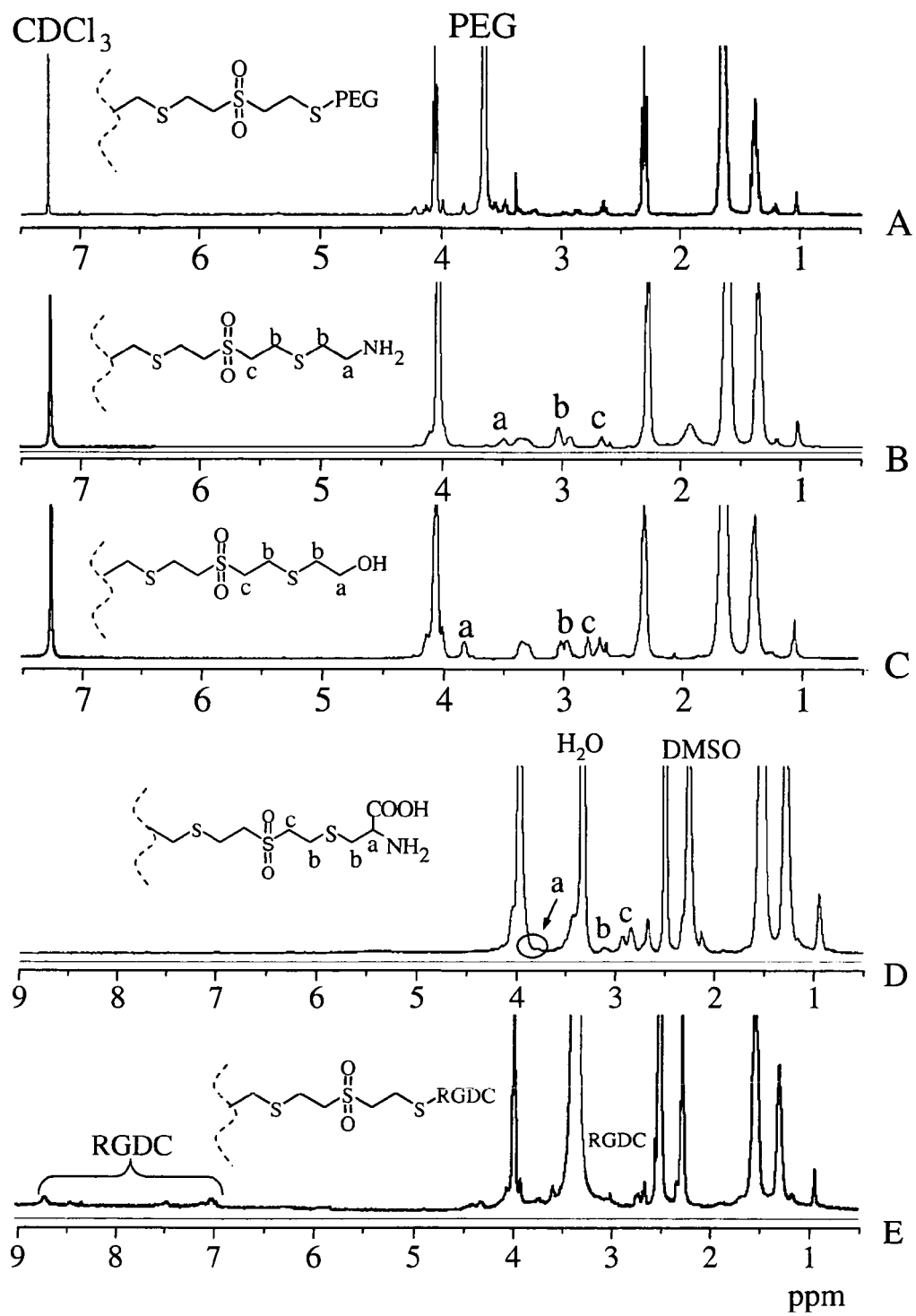
Fig.3 1H NMR spectra (400 MHz) of P(CL-co-AC)8.7% copolymer after modification with thiol-containing molecules. (A) PEG-SH (CDCl3), (B) 2-mercaptoethylamine (CDCl3), (C) 2-mercaptoethanol (CDCl3), (D) L-cysteine (DMSO-d6), and (E) RGDC (DMSO-d6).

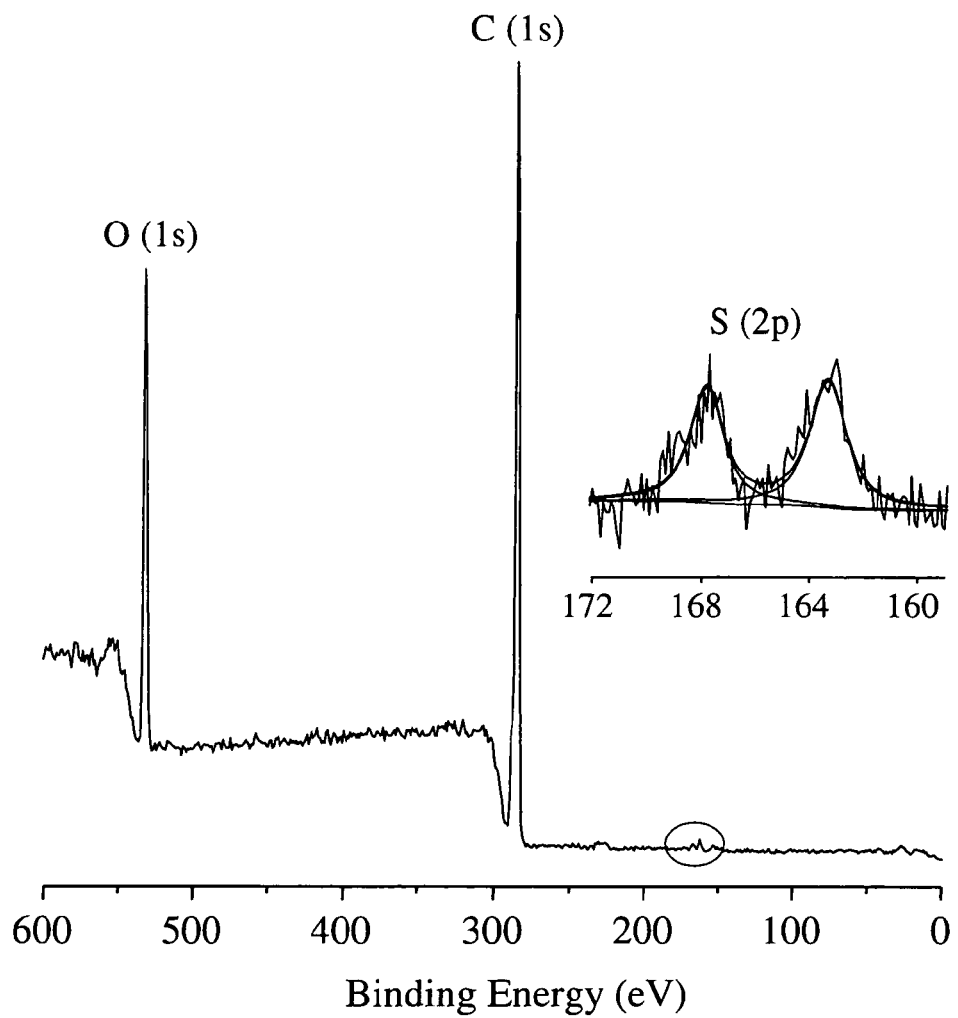
Fig.4 The XPS spectrum of P(CL-co-VSC)4.2%. The insets show the signals of S 2p with curve fitting.

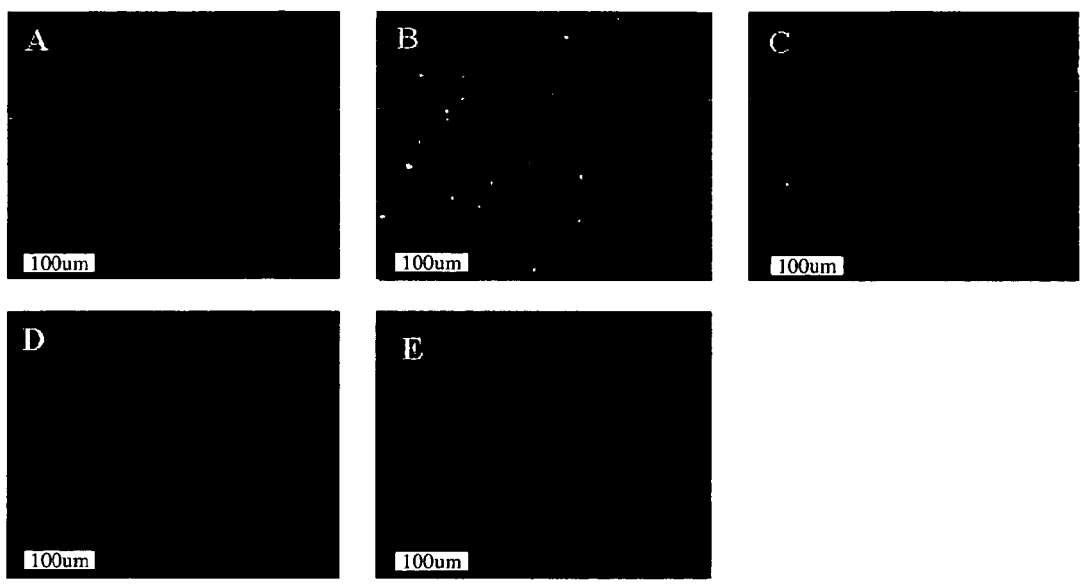
Fig.5 Fluorescence images of VS-functionalized biodegradable polymer films after successive treatment with cystamine and FITC in aqueous condition. (A) P(CL-co-VSC)4.2%, (B) P(CL-co-VSC)8.7%, (C) P(CL-co-VSC)34.5%, (D) P(LA-co-VSC)3.5%, (E) P(TMC-co-VSC)3.5%.

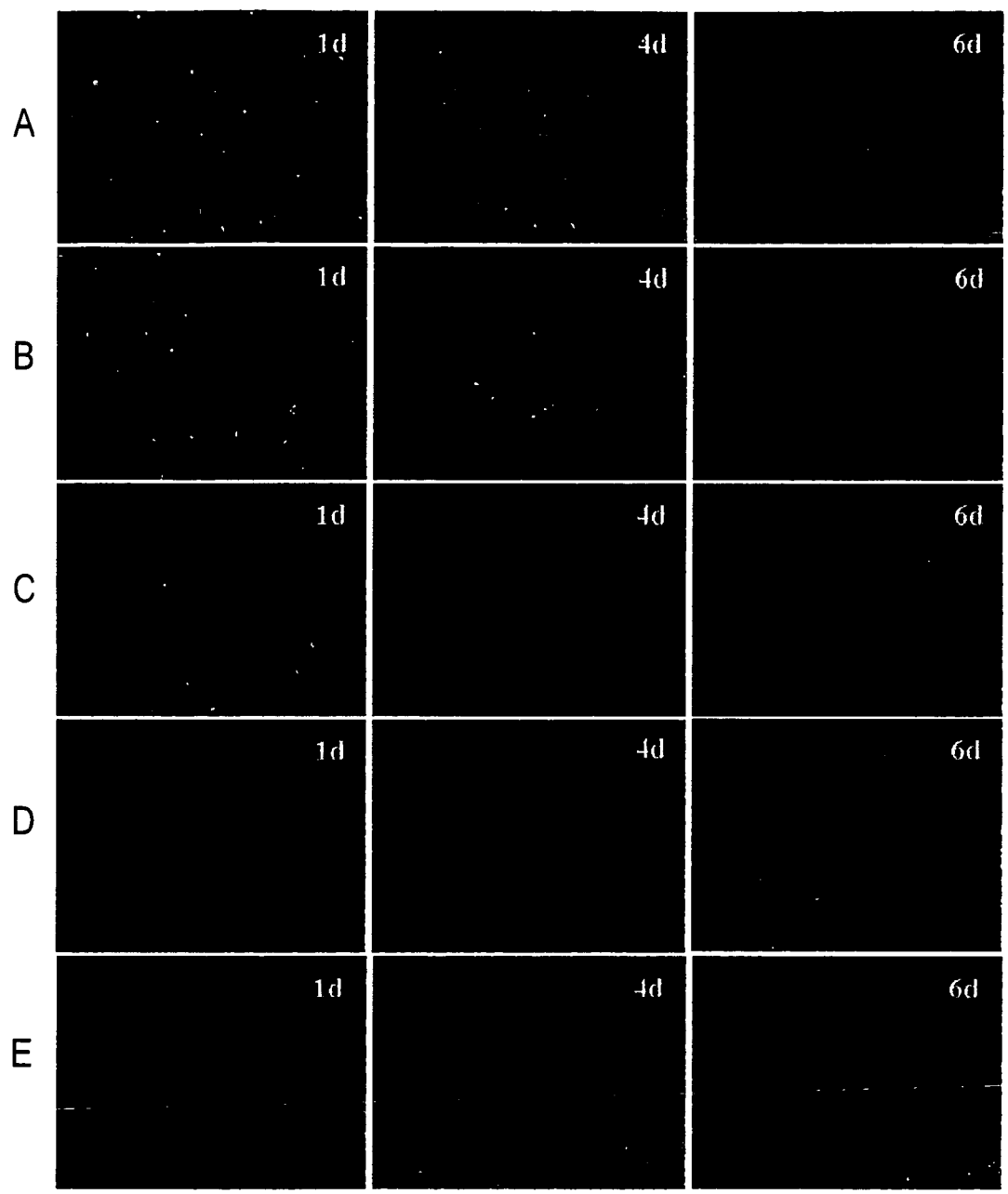
Fig.6 Images (×50) of MG63 cells cultured on the unmodified and modified P(CL-co-VSC)8.7% films for 1, 4 and 6 d. (A) unmodified P(CL-co-VSC)8.7% film, (B) PEG-SH modified film, (C) GC-SH modified film, (D) RGDC modified film, and (E) tissue culture plastic (blank control).

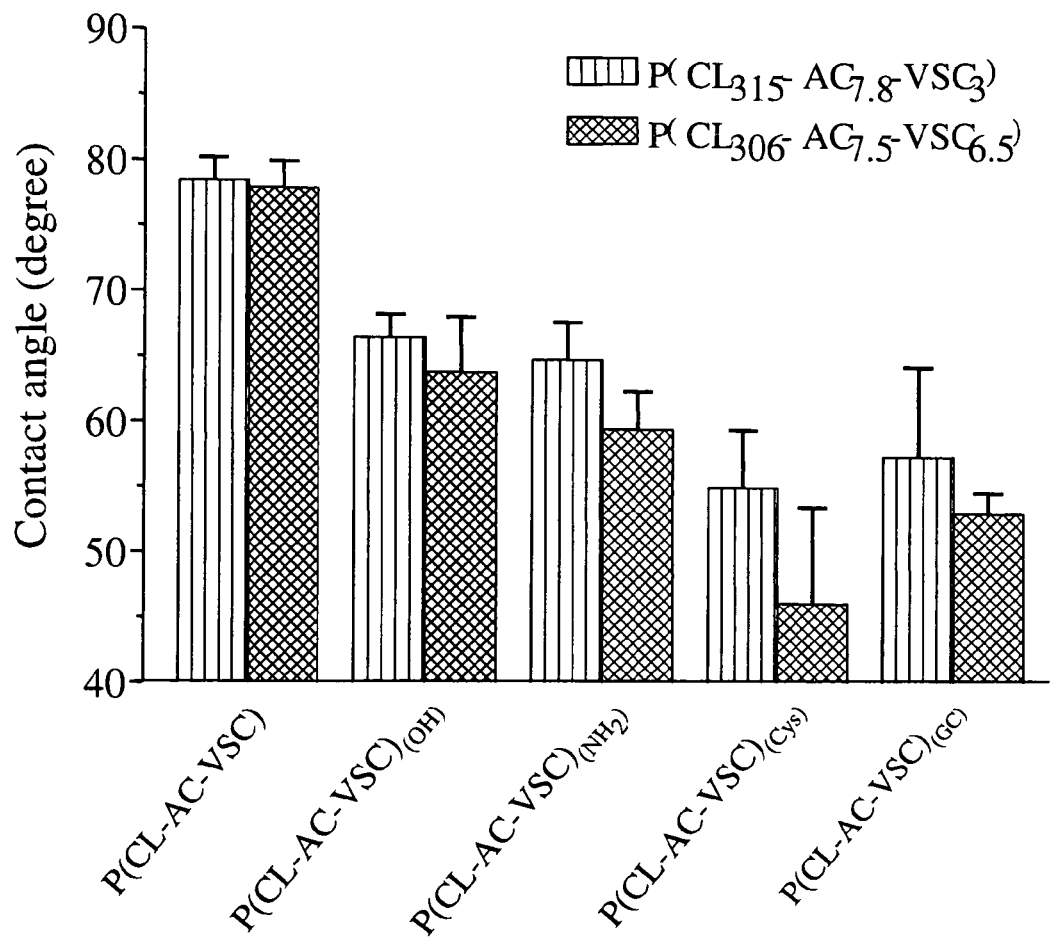
Fig.7 Contact angle of coatings modified with thiol-containing molecules.

METHOD FOR MAKING A POLYMER, A POLYMER ARTICLE, A BIODEVICE, AND CYCLIC CARBONATE

CROSS-REFERENCE TO RELATED APPLICATIONS

This is a U.S. national stage application of International Patent Application No. PCT/EP2011/061256, filed Jul. 4, 2011.

The present invention relates to a method for making polymer wherein a cyclic (alkyl) carbonate is incorporated in to the polymer chain by ring opening polymerisation, to the polymer produced, to a polymer article formed with such polymer, to a biodevice incorporating the polymer or polymer article, and the cyclic (alkyl) carbonate used in the polymerisation.

The ever growing biomedical technology such as tissue engineering, regenerative medicine and controlled drug release intimately relies on the development of advanced functional biomaterials. Aliphatic polyesters and polycarbonates due to their unique biocompatibility, biodegradability and approved use in biodevices by the US food and drug administration (FDA) are the prime synthetic biomaterials. For example, they have been applied for absorbable orthopedic devices, microparticles for controlled protein release, cell and tissue scaffolds, as coatings in drug-eluting stents, and nanoparticles for targeted drug release. However, common biodegradable polymers are often challenged by their high hydrophobicity, improper degradation profile, and in particular by their (surface) properties such as the absence of reactive centers for the covalent immobilization of bioactive molecules such as drugs, peptides, proteins and non-fouling polymers. This "inert" nature has largely hampered the design of biologically active polymer articles using the polymers. In the past decade, significant efforts have been directed to the development of functional aliphatic polyesters and polycarbonates, containing e.g. hydroxyl, carboxyl, amine, allyl, alkyne/azide, and acryloyl pendant groups. The post-polymerization modification based on these functional polymers may provide entry to a variety of sophisticated materials, coatings and devices.

The present invention has for its object the development of functional biodegradable polymers in which polymer synthesis does not involve protection and deprotection procedures and post-polymerization modification proceeds quantitatively under mild conditions without aid of any toxic catalyst and without generation of any by-product. In this way, polymer degradation as well as possible contamination with toxic catalysts and byproducts may be prevented.

The present invention is based on the sight that cyclic (alkyl) carbonates having a functional group reactive with a sulfhydryl group are advantageous for producing polymers that are modified with thiolated molecules. Such functional group advantageously exhibits a low reactivity towards radical polymerization, and high hydrophilic nature. Thus, the use of such sulfhydryl reactive functional groups in a polymer might overcome problems associated with acryloyl functional groups and may enable direct modification of the corresponding polymer articles, such as polymer films, in an aqueous medium. In relation to the last remark it is noted that there is a long felt need for modifying polymers and polymer articles and coatings that preferably takes place in aqueous conditions without the help of a catalyst.

Accordingly, the present invention provides a method for making a polymer wherein during ring opening polymerisation is incorporated into the polymer chain at least one cyclic (alkyl) carbonate monomer having the formula (1)

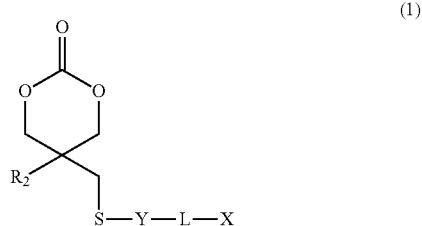

wherein Y is optional and represents the residue of a sulfhydryl reacted group, X represents a functional group reactive with a sulfhydryl group, L=—[CH2]n with n=0-10, or L= —[CH2]p-S—S—[CH2]q with p and q are 0-5 or L=-[PEG]- with PEG is a group that comprises a —[CH2CH2O]m- group with m=1-200, and R2 is hydrogen, methyl or ethyl.

The functional group X shows a high reactivity and selectivity towards the addition with a thiolated or sulfhydryl comprising ligand, and does not substantially affect the ring opening polymerisation. In addition, the addition reaction with the sulfhydryl group of the ligand may be carried out before and/or after the ring opening polymerisation.

BRIEF DESCRIPTION OF THE FIGURES

FIG. 1 shows the 1 H NMR spectra (400 MHz, CDCl₃) of vinyl sulfone-diol (A) and of vinyl sulfone carbonate (VSC) (B);

FIG. 2 shows the 1 H NMR spectra (400 MHz, CDCl₃) of vinyl sulfone (VS) functionalized biodegradable polymers. (A) copolymer of ϵ-caprolactone (CL) and vinyl sulfone carbonate (VSC): P(CL-co-VSC); (B) copolymer of lactide (LA) and vinyl sulfone carbonate (VSC): P(LA-co-VSC); (C) copolymer of trimethylenecarbonate (TMC) and vinyl sulfone carbonate (VSC): P(TMC-co-VSC).

FIG. 3 shows the 1 H NMR spectra (400 MHz) of copolymer of ϵ-caprolactone (CL) and acryloyl carbonate (AC): P(CL-co-AC) 8.7% copolymer, after modification with thiol-containing molecules. (A) PEG-SH (CDCl₃), (B) 2-mercaptoethylamine (CDCl₃), (C) 2-mercaptoethanol (CDCl₃), (D) L-cysteine (DMSO-d6), and (E) arginine-glycine-aspartic acid-cysteine peptide (RGDC) (DMSO-d6).

FIG. 4 shows the XPS spectrum of copolymer of ϵ-caprolactone (CL) and vinyl sulfone carbonate (VSC): P(CL-co-VSC) 4.2%. The insets show the signals of S 2p with curve fitting.

FIG. 5 show fluorescence images of vinyl sulfone functionalized biodegradable polymer films after successive treatment with cystamine and Fluorescein isothiocyanate (FITC) in aqueous condition. (A) P(CL-co-VSC) 4.2%, (B) P(CL-co-VSC) 8.7%, (C) P(CL-co-VSC) 34.5%, (D) P(LA-co-VSC) 3.5%, (E) P(TMC-co-VSC) 3.5%.

FIG. 6 shows images (×50) of MG6₃ cells cultured on the unmodified and modified P(CL-co-VSC)8.7% films for 1, 4 and 6 d. (A) unmodified P(CL-co-VSC) 8.7% film, (B) PEG-SH modified film, (C) GC-SH modified film, (D) RGDC modified film, and (E) tissue culture plastic (blank control).

FIG. 7 shows the contact angle of coatings modified with thiol-containing molecules.

According to a first embodiment of the method according to the invention is the cyclic (alkyl) carbonate monomer cyclic (alkyl) vinyl sulfone carbonate having formula (2)

(2)

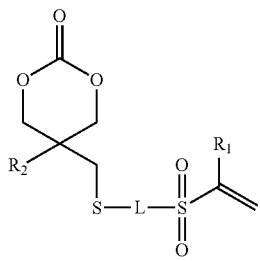

wherein $R_1$ is hydrogen, $R_2$ has the above identified meaning, and L represents a —$CH_2CH_2$— group (see for instance the compound of formula (2A)), or a —$CH_2CH_2SO_2$-PEG-group (see for instance the compound of formula (2B)), (2A)

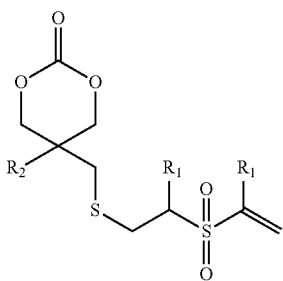

(2B)

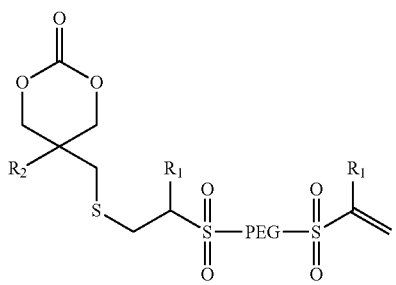

wherein $R_1$ is hydrogen, methyl or ethyl and $R_2$, and PEG have the above identified meaning. The monomers with the formula (2A) and of the formula (2B) may be produced by a reaction of the cyclic carbonate thiol with divinyl sulfone or bifunctional PEG vinylsulfone.

Such pendant vinyl sulfone group is very suitable for direct modification of the monomer, the polymer formed by ring opening polymerisation, and the polymer article made with the polymer. For such modification a catalyst is generally not required whereas the reaction may be carried out under mild, aqueous conditions.

The PEG group may have in general any length as long as the ring opening polymerisation and/or modification is not substantially negatively affected. This means that for the ring opening polymerisation the length is preferably limited to n is 1 to 20, more preferably 1 to 10.

One or more pegylated cyclic (alkyl) carbonates may be used that are capped with non-functional groups, such as an alkoxy group like a methoxy group. The incorporation of such pegylated carbonates increases the hydrophilicity of the (co) polymer although they do not participate in a modification treatment. The amount of such pegylated cyclic carbonate to be introduced in the (co)polymer may be selected on the basis of the desired degree of hydrophilicity of the (co)polymer.

According to another preferred embodiment, the monomer is a pegylated cyclic (alkyl) carbonate having the formula (3)

(3)

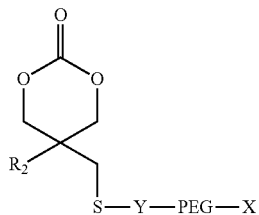

wherein Y represents the residue of a sulfhydryl reacted group, X represents a functional group reactive with a sulfhydryl group, and $R_2$ and PEG have the above identified meaning. Such a pegylated carbonate may be produced by reacting a mercapto diol or a thiol cyclic carbonate with the reactant Y'-PEG-X, wherein the functional group Y' is reactive with a sulfhydryl group. The functional group Y' is preferably the same as the group X. This (when the group Y' is different from the group X) avoids side products in which undesired the group X and not the group Y' has reacted with the sulfhydryl group of the cyclic carbonate.

According to a preferred embodiment of the invention the pegylated cyclic (alkyl) carbonate monomer may be selected from very suitable cyclic (alkyl) carbonate monomers independently selected from the group comprising:

i. the monomer of formula (1A)

(1A)

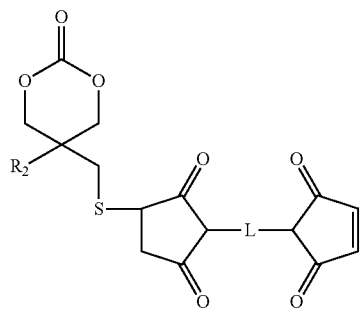

ii. the monomer of formula (1B)

(1B)

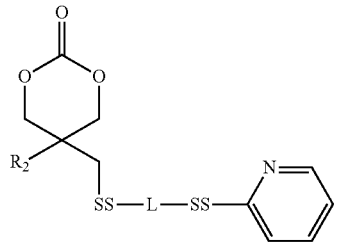

iii. the monomer of formula (1C)

(1C)

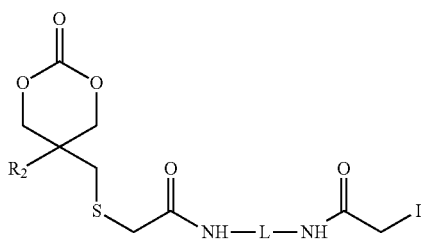

vii the monomer of formula (1D)

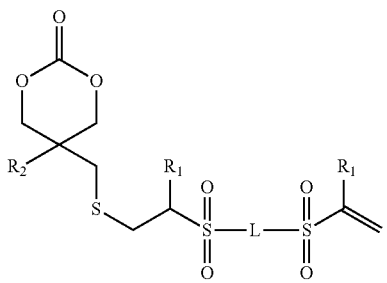

(1D)

Wherein $R_1$, $R_2$ and L have the above identified meaning. These monomers may be produced by a reaction between the corresponding cyclic carbonate thiol with a corresponding bifunctional L based reactant, such as a maleimide, orthopyridyl-disulfide, iodoacetamide, and divinyl sulfone, respectively.

A more preferred group comprises pegylated cyclic (alkyl) carbonates such as independently be selected from the group comprising:

i. the monomer of formula (3A)

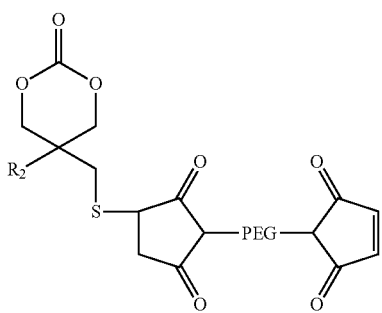

(3A)

the monomer (3A) may be produced by a reaction of the cyclic carbonate thiol with a bifunctional PEG maleimide.

ii. the monomer of formula (3B)

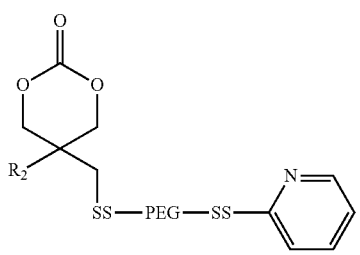

(3B)

the monomer (3B) may be produced by a reaction of the cyclic carbonate thiol with a bifunctional PEG orthopyridyl-disulfide.

iii. the monomer of formula (3C)

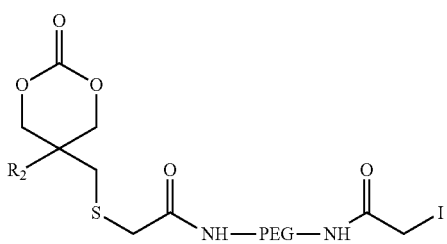

(3C)

wherein $R_2$ and PEG has the above identified meaning. The monomer (3C) may be produced by a reaction of the cyclic carbonate thiol with a bifunctional PEG iodoacetamide, respectively.

The method according to the invention is thus characterised in that the polymer is an (alkyl) polycarbonate or copolycarbonate thereof, comprising the steps of: providing at least one monomer of a cyclic (alkyl) carbonate having the formula (1) wherein $R_2$ is hydrogen, methyl or ethyl, and X is a functional group reactive with sulfhydryl group; and polymerising by ring opening polymerisation the monomer or monomers thereby making as the polymer the sulfhydryl reactive polycarbonate or copolycarbonate.

According to a very advantageous method of the invention the method comprises making a polymer wherein during the polymerisation at least one (alkyl) vinyl sulfone group is incorporated in the polymer chain by ring opening polymerisation of at least a cyclic (alkyl) vinyl sulfone carbonate having the formula (2A) and/or pegylated cyclic (alkyl) vinyl sulfone carbonate having the formula (2B):

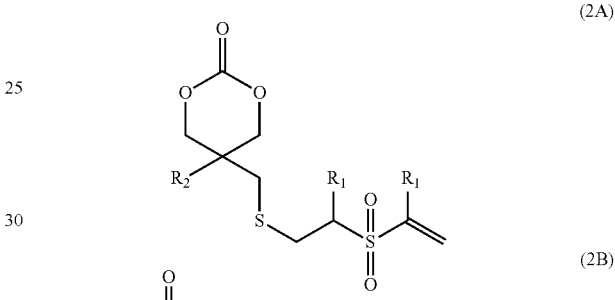

(2A)

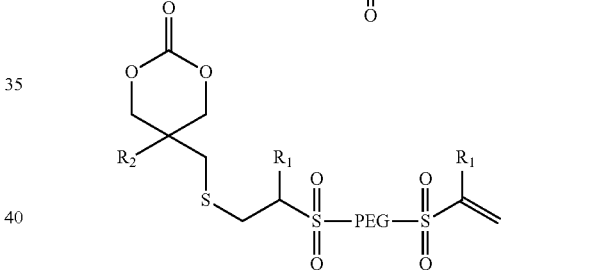

(2B)

wherein $R_1$ and $R_2$ each independently are hydrogen, methyl or ethyl.

It is apparent that the polymer according to the invention comprises a functional group reactive with a sulfhydryl group such as a vinyl sulfone group, iodoacetamide group, maleimide group, and orthopyridyl-disulfide group, as pendant groups that are suitable for modification with a ligand. However, it will be evident that during monomer synthesis other sulfhydryl reactive functional groups may be used as long as there is no undesired interference with either the ring opening polymerisation or (where appropriate) the formation of the cyclic carbonate. The modification may be carried out by any suitable reaction, such as through selective Michael-type conjugate reaction with thiol-containing molecules, such as 2-mercaptoethanol, cystamine, cysteine, GRGDC, PEG-SH, and the like, and also with an amine- containing molecule, such as 2-amino ethanol. The PEG linker group present in the cyclic carbonate of formula (2) further increases the hydrophilicity of the polymer without interfering with the polymerization and optionally modifications and crosslinking. This implies that the PEG should be non-reactive under the envisaged reaction conditions for the various reactions (for instance OH-groups should be absent), and should be of relatively short length (such as $M_n(PEG)<200$), so that the polymerization is not substantially negatively affected.

However, it is noted that pegylation of the polymer may also be carried out after the ring opening polymerisation and then the length of the PEG group may be larger. In addition, the PEG group represents any type of PEG group such as straight or branched PEG groups which may be mono functional or polyfunctional.

According to a preferred embodiment, the polymer may be a homopolymer, such as an (alkyl)vinyl sulfone polycarbonate homopolymer or a pegylated (alkyl) vinyl sulfone polycarbonate, or copolycarbonate thereof. Thereto the method of the invention comprises the step of (i) providing at least one monomer of a cyclic (alkyl) vinyl sulfone carbonate having the formula (1) and/or pegylated cyclic (alkyl) vinyl sulfone carbonate having the formula (2), and the step (ii) of polymerising the monomer or monomers thereby making as the polymer an (alkyl)vinyl sulfone polycarbonate or a pegylated (alkyl)vinyl sulfone copolycarbonate.

According to another and preferred embodiment the polymer may be a copolymer with a cyclic(alkyl) acryloyl carbonate. Thereto the method comprises in step (i) the addition of a cyclic (alkyl) acryloyl carbonate having the formula (4)

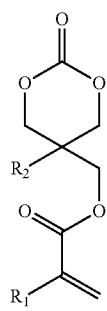

(4)

wherein R1 and R2 each independently are hydrogen, methyl or ethyl. Accordingly is formed as the polymer an (alkyl)vinyl sulfone acryloyl copolycarbonate. This copolymer comprises pendent acryloyl groups that are very suitable (better than the pendant vinyl sulfone group) for crosslinking and grafting for instance by photo irradiation. Thus, it will be possible to crosslink the copolymer produced, the polymer article, such as a polymer film, produced as well as the crosslinked products of both. Thereby are improved the properties of the polymer and polymer articles.

According to a further preferred embodiment, the polymerization may further comprise an additional monomer (besides the (alkyl) acryloyl carbonate). This allows for the provision of versatile polymers that are biodegradable and may be modified, crosslinked and incorporated in many different biodevices and biomaterials. Accordingly, it is preferred that in the polymerization is added an additional monomer selected from the group comprising a cyclic $C_3$-$C_{14}$-alkylester having the formula (5)

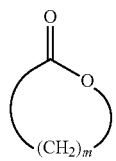

(5)

m=3-14, such as δ-valerolactone, ε-caprolactone and ω-pentadecalactone;

a cyclic diester having the formula (6)

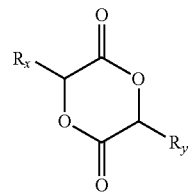

(6)

wherein $R_x$ and $R_y$ each independently are hydrogen, methyl or ethyl, such as lactide;

a morpholinedione having the formula (7)

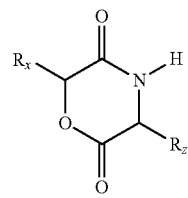

(7)

wherein $R_x$ is hydrogen, methyl or ethyl and independently $R_z$ is hydrogen, methyl, ethyl, or an amino acid residue which residue is optionally protected;

a dioxanone having the formula (8)

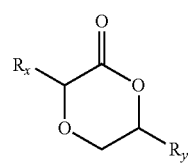

(8)

wherein $R_x$ and $R_y$ each independently are hydrogen, methyl or ethyl; and/or a cyclic $C_3$-$C_5$-alkylcarbonate having the formula (9)

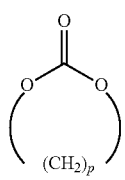

(9)

wherein p=3-5, such as trimethylenecarbonate.

The (alkyl) polycarbonates, such as the (alkyl) vinyl sulfone based polymers, are biodegradable and may be used in vastly different structures and compositions and can be readily prepared without protection and deprotection steps. Any post-polymerization modification with thiol-containing molecules and/or amine-containing molecules proceeds in a quantitative manner under extremely mild conditions (in the absence of catalyst), minimizing possible degradation and contamination. Also the Michael-type addition of the vinyl sulfone groups with thiol- and amine-containing molecules is highly selective and tolerant to a variety of functional groups including hydroxyl, carboxyl, and amine, enabling facile conjugation of different types of biologically active molecules. For the modification are available functional group X, such as the (alkyl) vinyl sulfone group, the pegylated (alkyl) vinyl sulfone group, the maleimide group, iodoacetamide group, the sulfhydryl-disulfide group, and optionally the (alkyl) acryloyl group. The modification proceeds with a so called functional ligand. Preferably, the modification comprises a reaction with a thiol-containing functional ligand and/or with an amine-containing functional ligand, and preferably the thiol-containing functional ligand is 2-mercaptoethanol, 3-mercaptopropanoic acid, cysteamine, cysteine, and arginine-glycine-aspartic acid-cysteine (RGDC) peptide, a mercapto saccharide, PEG-SH and/or preferably the amine-containing functional ligand is 2-amino ethanol or amino-PEG-SH.

Again it is emphasized that biodegradable devices and coatings based on the polymers of the invention allow for the first time direct and robust surface modification with thiol- and amine-containing molecules in aqueous conditions in the absence of catalyst. The makes the polymers prone to surface functionalization of medical implants as well as cell and tissue scaffolds.

As indicated above, the preferred but optional presence of an (alkyl) acryloyl pendant group or groups provide the possibility of effective crosslinking by a reaction with the acryloyl group. This crosslinking may comprise crosslinking by photo-crosslinking, and/or by gamma irradiation of the (alkyl) acryloyl group. For polymers that contain a mixture of (alkyl) acryloyl and other sulfhydryl reactive groups, the acryloyl groups can be crosslinked selectively. Crosslinking is also possible via the other sulfhydryl reactive groups by a reaction with a di-thiol, a di-amine, and/or an aminothiol such as 1,6-hexanedithiol, ethylene diamine, 2-mercaptoethylamine. Advantageously, the crosslinking may be carried out on either the (functionalised and/or modified) polymer of the invention or on a polymer article, such as a film made thereof.

In relation to the polymerisation it is noted that the polymerisation may be a random polymerisation or block copolymerisation comprising at least two polymer blocks, such as of each monomer. The polymerisation may result in a formed or structured polymer if preferably the polymerisation is performed with a multifunctional polymerisation initiator having a linear shape, branched shape, or star shape, and preferably the multifunctional polymerisation initiator is a multifunctional PEG.

Another aspect of the invention relates to a polymer or polymer article obtainable by the method according to the invention, to a biodevice, such as a stent, blood vessel, and cell compartment, comprising a polymer of the invention or having been made using at least one polymer according to the invention. Such biodevice may comprise the polymer of the invention bound to a hydrogel, preferably comprising a biologically active agent, such as drug, a protein, (oligo)-peptide, an aptamer, a nucleic acid such as DNA and RNA, an anticoagulant, a non-fouling agent, an antibody or an enzyme, and combinations thereof. Evidently, the polymer of the invention may be used in making biodevices, and/or for use in medicine.

A further aspect of the invention relates to polymer mixtures and articles that are made of polymer mixtures that include a polymer according to the invention.

Finally, the present invention relates to cyclic (alkyl) carbonates having:

i. the formula (1)

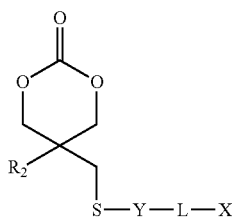

(1)

wherein Y is optional and represents the residue of a sulfhydryl reacted group, X represents a functional group reactive with a sulfhydryl group, L=—[CH2]n with n=0-10, or L=—[CH2]p-S—S—[CH2]q with p and q are 0-5 or L=-[PEG]- with PEG is a group that comprises a —[CH2CH2O]m- group with m=1-200, and R2 is hydrogen, methyl or ethyl.

ii. the formula (2)

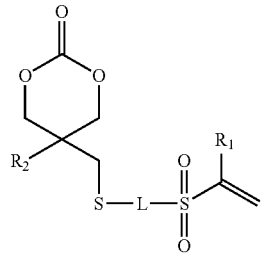

(2)

wherein $R_1$ is hydrogen, $R_2$ has the above identified meaning, and L represents a —$CH_2CH_2$— group, or a —$CH_2CH_2SO_2$-PEG-group, wherein PEG represents an agent comprising at least one —$[CH_2CH_2O]_n$— group, wherein n is 1-200;

iii. the monomer of formula (1A)

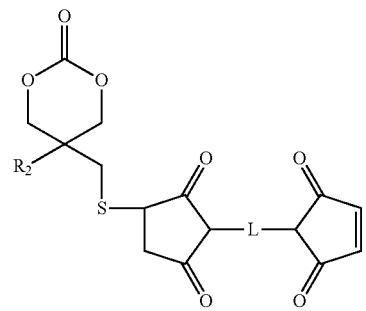

(1A)

iv. the monomer of formula (1B)

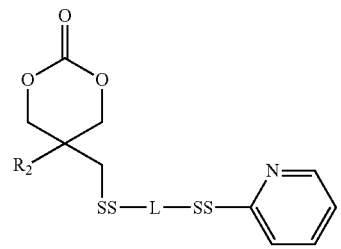

(1B)

v. the monomer of formula (1C)

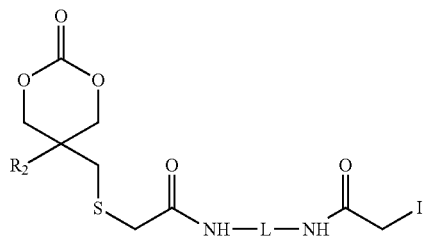

(1C)

vii the monomer of formula (1D)

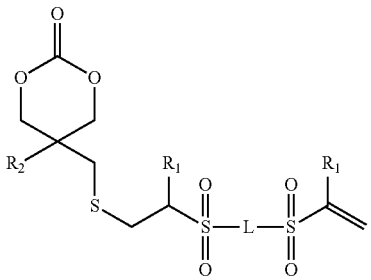
(1D)

Wherein $R_1$ is hydrogen, methyl or ethyl and $R_2$ and L have the above identified meaning;

vi. the formula (3)

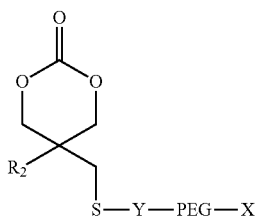
(3)

wherein Y represents a sulfhydryl reactive group, X represents a functional group reactive with sulfhydryl group, and $R_2$ and PEG have the above identified meaning, and preferably of formula (3A)

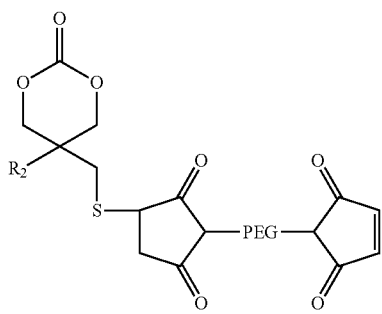
(3A)

or formula (3B)

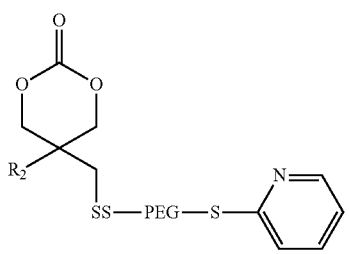
(3B)

and/or of formula (3C)

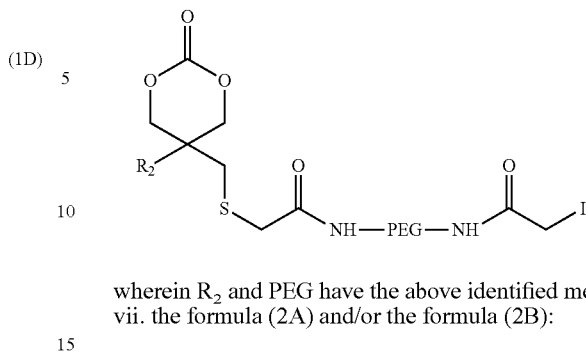
(3C)

wherein $R_2$ and PEG have the above identified meaning, vii. the formula (2A) and/or the formula (2B):

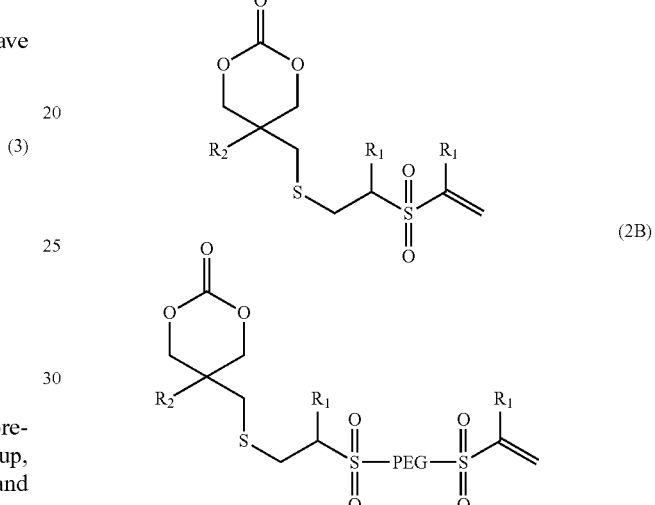
(2A)

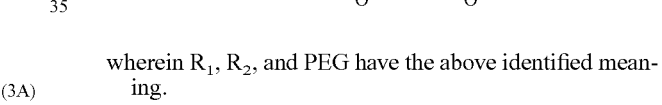
(2B)

wherein $R_1$, $R_2$, and PEG have the above identified meaning.

Mentioned and other features of the polymers, polymer coating, polymer article and use according to the invention will be further elucidated by various examples which are only given for information purposes and not intended to limit the invention in any aspect. Thereto reference will be made to the schemes, tables and figures.

EXAMPLE 1

Synthesis of Methyl Vinyl Sulfone Carbonate Monomer

In this synthesis the following agents have been used: 3-methyl-3-oxetanemethanol (97%, Alfa), hydrobromic acid (40%, SCRC), sodium hydrosulfide hydrate (68%, Acros), divinyl sulfone (95%, Dalian Guanghui, China), triethylamine ($Et_3N$, 99%, Alfa Aesar), stannous octoate ($Sn(Oct)_2$, 95%, Sigma), 2-mercaptoethanol (>99%, Amresco), 2-mercaptoethylamine hydrochloride (99%, Alfa Aesar), and L-cysteine (>99%, Alfa Aesar), fluorescein isothiocyanate (FITC, 98%, Sigma) were used as received. GRGDC was purchased from Suzhou China Tech Peptide Co., Ltd. Thiolated glycol chitosan (GC-SH, $M_n$=80000, DS=6.85) and thiolated PEG (PEG-SH, $M_n$=5000) were synthesized according to previous reports [1, 2]. Ethyl chloroformate (>96%, SCRC) was distilled prior to use. Isopropanol and ε-caprolactone (ε-CL, 99%, Alfa Aesar) were dried over $CaH_2$ and distilled before use. Toluene was dried by refluxing over sodium wire under an argon atmosphere prior to distillation. L-lactide (L-LA, >99%, Purac) and trimethylene carbonate (TMC, Jinan Daigang Co. Ltd., China) were recrystallized from dry toluene.

For the characterization $^1$H NMR spectra were recorded on the Unity Inova 400 operating at 400 MHz. CDCl$_3$ and DMSO-d$_6$ were used as solvents and the chemical shifts were calibrated against residual solvent signals. The molecular weight and polydispersity of the copolymers were determined by a Waters 1515 gel permeation chromatograph (GPC) instrument equipped with two linear PLgel columns (500 Å and Mixed-C) following a guard column and a differential refractive-index detector. The measurements were performed using THF as the eluent at a flow rate of 1.0 mL/min at 30° C. and a series of narrow polystyrene standards for the calibration of the columns. The static water contact angle measurements were performed on an SL-200C optical contact angle meter (Solon Information Technology Co.) using the sessile drop method.

X-ray photoelectron spectroscopy (XPS) measurements were carried out on a Kratos AXIS UltraDLD instrument equipped with an evaporation chamber (base pressure<5× 10$^{-10}$ Torr) and an analysis chamber (3×10$^{-10}$ Torr). XPS analysis was undertaken under high vacuum on films prepared on silicon wafers (0.076 Ω/□, in which □ means square). The samples were irradiated with monochromatic Al-Ka (hv=1486.6 eV, spot size 400 μm×700 μm) and a take-off angle of 45° with respect to the sample surface. All spectra were measured at room temperature and calibrated by setting the C 1s (C—C) peak at 284.5 eV.

Vinyl Sulfone Carbonate (VSC) monomer was synthesized in four steps (Scheme 1). First, HBr (40%, 40 mL) was dropwise added to a solution of 3-methyl-3-oxetanemethanol (10.2 g, 0.10 mol) in THF (100 mL) under stirring at 0° C. The reaction mixture was warmed to 25° C. and stirred for 5 h. The reaction mixture was then diluted with H$_2$O (150 mL) and extracted with diethyl ether (4×150 mL). The organic phase was dried over anhydrous MgSO$_4$ and concentrated to give the desired product (bromo-diol) as a white solid (16.38 g, 90%). $^1$H NMR (400 MHz, CDCl$_3$): δ 3.68 (s, 4H, —C(CH$_2$OH)$_2$), 3.55 (s, 2H, —CH$_2$Br), 2.13 (s, 2H, —(OH)$_2$), 0.93 (s, 3H, —CH$_3$).

Scheme 1. Synthetic pathway for VSC monomer. Conditions: (i) THF, dropwise addition of 40% HBr at 0° C., then 25° C. for 5 h.,; (ii) NaSH, 75° C., 17 h., DMF; (iii) divinyl sulfone, 30° C., methanol; (iv) ethyl chloroformate, Et$_3$N, 0° C., 4 h., THF.

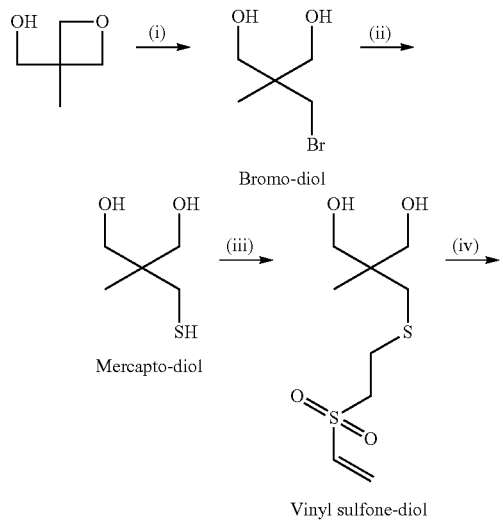

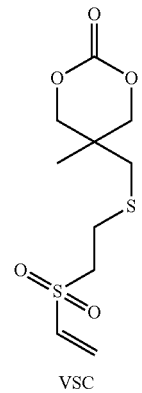

VSC

To a solution of bromo-diol (16.38 g, 0.09 mol) in DMF (150 mL) under stirring was added NaSH (22.23 g, 0.27 mol). The reaction mixture was stirred at 75° C. for 17 h, cooled to 25° C., diluted with D.I. water (1.0 L), and extracted with EtOAc (3×250 mL). The organic phase was dried over anhydrous MgSO$_4$ and concentrated. Residual DMF was removed by distillation under reduced pressure to yield mercapto-diol as a yellowish oil (5.26 g, 43%). $^1$H NMR (400 MHz, CDCl$_3$): δ 3.64 (s, 4H, —C(CH$_2$OH)$_2$), 2.67 (d, 2H, —CH$_2$SH), 2.27 (s, 2H, —(OH)$_2$), 1.31 (t, 1H, —SH), 0.85 (s, 3H, —CH$_3$).

To a solution of divinyl sulfone (10 mL, 99.6 mmol) in MeOH (350 mL) under stirring was dropwise added mercapto-diol (5.26 g, 38.7 mmol) at room temperature. The reaction mixture was warmed to 30° C. and stirred overnight in the dark. The solution was concentrated under reduced pressure and the residue was purified by column chromatography (eluent: ethyl acetate/petroleum ether=4/1, v/v) to yield vinyl sulfone-diol (5.89 g, 60%). $^1$H NMR (400 MHz, CDCl$_3$): δ 6.23~6.64 (m, 3H, —CH═CH$_2$), 3.64 (s, 4H, —C(CH$_2$OH)$_2$), 3.27 (m, 2H, —SCH$_2$CH$_2$—), 2.95 (m, 2H, —SCH$_2$CH$_2$—), 2.75 (s, 2H, —CCH$_2$S—), 2.49 (s, 2H, —(OH)$_2$), 0.85 (s, 3H, —CH$_3$), see FIG. 1A.

To a solution of vinyl sulfone-diol (5.89 g, 23.2 mmol) and ethyl chloroformate (4.6 mL, 48.7 mmol) in dry THF (200 mL) at 0° C. under stirring was dropwise added a solution of Et$_3$N (7 mL, 51.1 mmol) in THF (5 mL). The reaction was allowed to proceed for 5 h at 0° C. The reaction mixture was filtered and the filtrate was concentrated under reduced pressure. The crude product was recrystallized from THF to yield vinyl sulfone carbonate monomer (4.61 g, 71%). $^1$H NMR (400 MHz, CDCl$_3$): δ 6.23~6.64 (m, 3H, —CH═CH$_2$), 4.17~4.26 (s, 4H, —C(CH$_2$)$_2$C—), 3.27 (m, 2H, —SCH$_2$CH$_2$—), 2.95 (m, 2H, —SCH$_2$CH$_2$—), 2.75 (s, 2H, —CCH$_2$S—), 1.10 (s, 3H, —CH$_3$). $^{13}$C NMR (400 MHz, CDCl$_3$): δ 145.21, 133.12, 129.27, 72.40, 51.67, 34.65, 30.17, 23.58, 15.75. Anal. Calcd for C$_{10}$H$_{16}$O$_5$S$_2$: C, 42.84; H, 5.75; S, 22.87. Found: C, 43.24; H, 5.70; S, 22.37. TOF-MS (m/z): calcd for C$_{10}$H$_{16}$O$_5$S$_2$ 280.0439. found 280.0231, see also FIG. 1B.

EXAMPLE 2

Synthesis of Ethyl Vinyl Sulfone Carbonate Monomer

Ethyl vinyl sulfone carbonate monomer (VSEC) was also synthesized in four steps (Scheme 2). To a stirred solution of 3-ethyl-3-oxetanemethanol (5.8 g, 50 mmol) in THF (100 mL) was dropwise added HBr (40%, 20 mL). The reaction mixture was allowed to warm to 25° C. and stirred for 5 h. The reaction mixture was then diluted with H$_2$O (150 mL) and extracted with diethyl ether (4×150 mL). The organic phase was dried over anhydrous MgSO$_4$ and concentrated to give the desired product (bromo-diol) as a white solid (8.82 g, 90%).

To a stirred solution of bromo-diol (8.82 g, 0.045 mol) in DMF (100 mL) was added NaSH (11.5 g, 140 mol). The reaction mixture was stirred at 75° C. for 17 h, cooled to 25° C., diluted with ultrapure water (500 mL), and extracted with EtOAc (3×200 mL). The organic phase was dried over anhydrous MgSO$_4$ and concentrated. Residual DMF was removed by distillation under reduced pressure to give mercapto-diol as viscous yellowish oil (2.7 g, 40%).

To a stirred solution of divinyl sulfone (5.4 mL, 54 mmol) in MeOH (100 mL) was dropwise added mercapto-diol (2.7 g, 18 mmol). The reaction mixture was allowed to warm to 30° C. and stirred overnight in the dark. The solution was concentrated under reduced pressure and the residue was purified by column chromatography (eluent: ethyl acetate/petroleum ether=4/1, v/v) to give the vinyl sulfone-diol (2.89 g, 60%).

To a stirred solution of vinyl sulfone-diol (2.89 g, 10.8 mmol) and ethyl chloroformate (2.3 mL, 22.68 mmol) in dry THF (100 mL) at 0° C. was dropwise added Et$_3$N (3.5 mL, 25.5 mmol) dissolved in THF. The reaction was allowed to proceed for 5 h at 0° C. The reaction mixture was filtered and the filtrate was concentrated under reduced pressure The crude product was purified by recrystallizing from THF to yield vinyl sulfone carbonate monomer (2.2 g, 70%).

Scheme 2. Synthetic pathway for VSEC monomer. Conditions: (i) 40% hydrobromic acid, 0° C., 5 h., THF; (ii) sodium hydrosulphide, 75° C., 17 h., DMF; (iii) divinyl sulfone, 30° C., methanol; (iv) ethyl cholorformate, Et$_3$N, 0° C., 4 h., THF.

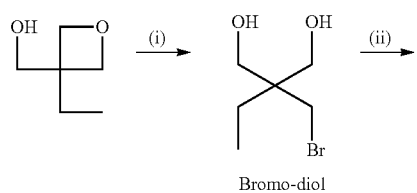

Bromo-diol

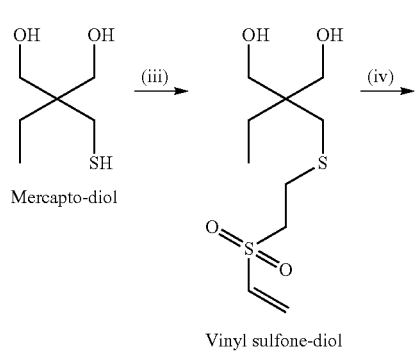

Mercapto-diol

Vinyl sulfone-diol

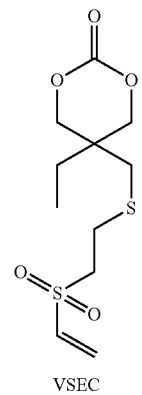

VSEC

EXAMPLE 3

Synthesis of Vinyl Sulfone Functionalized Polymers (Polyesters and Polycarbonates) According to the Invention The copolymerizations of VSC with ε-CL, L-LA and TMC were carried out in toluene at 110° C. for 1 d using isopropanol as an initiator and Sn(Oct)$_2$ as a catalyst. The following is a typical example of the synthesis of P(CL-co-VSC) 4.2% copolymer. In a glove box under a nitrogen atmosphere, to a solution of ε-CL (1.160 g, 10.18 mmol) and VSC (0.15 g, 0.54 mmol) in toluene (11 mL) under stirring were quickly added the stock solutions of isopropanol (4 mg, 0.06 mmol) and Sn(Oct)$_2$ (22 mg, 0.05 mmol) in toluene. The reaction vessel was sealed and placed in an oil-bath thermostated at 110° C. After 24 h polymerization, the reaction was terminated by two drops of acetic acid. A sample was taken for the determination of monomer conversion using $^1$H NMR. The resulting P(CL-co-VSC) copolymer was isolated by precipitation in ethanol, filtration and drying in vacuo, see Table 1. $^1$H NMR (400 MHz, CDCl$_3$, FIG. 2A): δ 6.23~6.64 (m, —CH═CH$_2$, PVSC), 5.01 (m, (CH$_3$)$_2$CH—), 4.05~4.13 (s, —CH$_2$O—, PCL; C(CH$_2$)$_2$O$_2$—, PVSC), 3.22 (m, SO$_2$CH$_2$—, PVSC), 2.86 (m, —CH$_2$S—, PVSC), 2.75 (s, —SCH$_2$C, PVSC), 2.30 (t, —COCH$_2$—, PCL), 1.64 (m, —CH$_2$CH$_2$CH$_2$—, PCL), 1.37 (m, —CH$_2$CH$_2$CH$_2$—, PCL), 1.22 (d, (CH$_3$)$_2$C—), 1.03 (s, —CH$_3$, PVSC).

TABLE 1

Synthesis of VS-functionalized biodegradable PCL through ring-opening copolymerization of ε-CL and VSC.[a]

| Entry | M/I[b] | $f_{VSC}$[c] (%) | $F_{VSC}$[d] (%) | $M_n \times 10^{-3}$ Theory | $^1$H NMR[e] | GPC[f] | PDI GPC[f] | Yield % |
|---|---|---|---|---|---|---|---|---|
| 1 | 100/1 | 5 | 4.8 | 12.2 | 11.3 | 17.7 | 1.78 | 84.8 |
| 2 | 160/1 | 5 | 4.2 | 20.9 | 19.8 | 26.4 | 1.34 | 91.5 |
| 3 | 320/1 | 5 | 4.1 | 39.1 | 36.4 | 46.7 | 1.66 | 95.0 |
| 4 | 150/1 | 10 | 8.7 | 19.6 | 18.1 | 21.0 | 1.50 | 80.0 |
| 5 | 150/1 | 20 | 16.3 | 22.0 | 19.4 | 21.3 | 1.62 | 81.4 |
| 6 | 120/1 | 40 | 34.5 | 21.6 | 19.5 | 24.0 | 1.80 | 78.6 |

[a]The copolymerization was carried out in toluene at 110° C. using isopropanol as an initiator and Sn(Oct)$_2$ as the catalyst for 1 d;
[b]Total monomer-to-initiator molar ratio;
[c]Molar fraction of VSC monomer in the feed;
[d]Molar fraction of VSC units in the resulting copolymer determined by $^1$H NMR;
[e]Estimated by $^1$H NMR end-group analysis;
[f]Determined by GPC (eluent: THF, flow rate: 1.0 mL/min, standards: polystyrene).

P(LA-co-VSC) and P(TMC-co-VSC) copolymers were synthesized in a similar manner, see Table 2. $^1$H NMR spectra as well as signal assignments of the copolymers were shown in FIGS. 2B and 2C. $^1$H NMR (400 MHz, CDCl$_3$) of P(LA-co-VSC): δ 6.23~6.64 (m, —CH═CH$_2$, PVSC), 5.16 (m, CH$_3$CH—, PLA), 4.05 (s, C(CH$_2$)$_2$O$_2$—, PVSC), 3.22 (m, SO$_2$CH$_2$—, PVSC), 2.86 (m, —CH$_2$S—, PVSC), 2.75 (s, —SCH$_2$C, PVSC), 1.58 (m, —CHCH$_3$, PLA), 1.22 (d, (CH$_3$)$_2$C—), 1.03 (s, —CH$_3$, PVSC). $^1$H NMR (400 MHz, CDCl$_3$) of P(TMC-co-VSC): δ 6.23~6.64 (m, —CH═CH$_2$, PVSC), 4.25 (s, —CH$_2$CH$_2$CH$_2$—, PTMC), 4.05 (s, C(CH$_2$)$_2$O$_2$—, PVSC), 3.22 (m, SO$_2$CH$_2$—, PVSC), 2.86 (m, —CH$_2$S—, PVSC), 2.75 (s, —SCH$_2$C, PVSC), 2.04 (s, —CH$_2$CH$_2$CH$_2$—, PTMC), 1.22 (d, (CH$_3$)$_2$C—), 1.22 (d, (CH$_3$)$_2$C—), 1.03 (s, —CH$_3$, PVSC).

TABLE 2

Synthesis of VS-functionalized PLA and PTMC through ring-opening copolymerization of LA or TMC with VSC.[a]

| Entry | copolymer | M/I[b] | $f_{VSC}$[c] (%) | $F_{VSC}$[d] (%) | $M_n \times 10^{-3}$ Theory | $^1$H NMR[e] | GPC[f] | PDI GPC[f] | Yield (%) |
|---|---|---|---|---|---|---|---|---|---|
| 1 | P(LA-co-VSC) | 140/1 | 5 | 3.5 | 21.1 | 20.2 | 58.3 | 1.67 | 91.3 |
| 2 | P(LA-co-VSC) | 300/1 | 5 | 3.4 | 45.2 | 39.8 | 86.2 | 1.56 | 70.6 |
| 3 | P(LA-co-VSC) | 130/1 | 10 | 7.4 | 20.5 | 18.5 | 40.1 | 1.71 | 88.1 |
| 4 | P(TMC-co-VSC) | 180/1 | 5 | 3.5 | 19.9 | 15.1 | 39.7 | 1.87 | 79.0 |

[a]The copolymerization was carried out in toluene at 110° C. using isopropanol as an initiator and Sn(Oct)$_2$ as the catalyst for 1 d;
[b]Total monomer-to-initiator molar ratio;
[c]Molar fraction of VSC monomer in the feed;
[d]Molar fraction of VSC units in the resulting copolymer determined by $^1$H NMR;
[e]Estimated by $^1$H NMR end-group analysis;
[f]Determined by GPC (eluent: THF, flow rate: 1.0 mL/min, standards: polystyrene).

EXAMPLE 4

Post-polymerization Modification of Vinyl Sulfone-functionalized Biodegradable Polymers The post-polymerization modification of VS-functionalized polymers was carried out using Michael-type conjugate addition reaction in DMF at room temperature under a nitrogen atmosphere. Various thiol-containing molecules (R-SH) including 2-mercaptoethanol, 2-mercaptoethylamine hydrochloride, L-cysteine, PEG-SH, GC-SH or GRGDC were employed. The SH/VS molar ratio was set at 2/1 and the reaction proceeded for 1 d. The modified polymers were isolated by precipitation from cold diethyl ether/ethanol (1/4, v/v) and dried in vacuo at room temperature. The $^1$H NMR spectra of thus modified P(CL-co-VSC) 8.7% are given in FIG. 3. It could be concluded that the modification was quantitative.

EXAMPLE 5

Preparation of Vinyl Sulfone Functionalized Biodegradable Films and Direct Modification with Thiol-containing Molecules Biodegradable films were prepared on the microscope slides using 0.2 wt. % solution of VS-functionalized copolymers in chloroform. The films, after thoroughly dried, were immersed in the phosphate buffered aqueous solution of a thiol-containing molecule (such as 2-mercaptoethanol, 2-mercaptoethyl amine hydrochloride, L-cysteine, PEG-SH, GC-SH, and GRGDC) at a concentration of 1 mg/mL for 24 h. The resulting modified films were thoroughly rinsed with deionized water and dried over phosphorus pentoxide under reduced pressure. The contact angles of both modified and unmodified films were determined on an SL-200C optical contact angle meter (Solon Information Technology Co.) using the sessile drop method. For XPS analysis, films were prepared on silicon wafers (0.076 Ω/□).

EXAMPLE 6

Fluorescence Observation on Cystamine-modified Films Treated with FITC

To confirm the immobilization of cystamine to VS-functionalized degradable polymer films and to test the chemical reactivity of the amine groups at the surface, cystamine-functionalized PCL film was further treated with FITC in phosphate buffered saline (PBS, 20 mM, pH 9.0) and then visualized with fluorescence microscopy. Briefly, VS-functionalized degradable polymer films following treatment with cystamine as above described were immersed in 0.5 mg/mL FITC solution in phosphate buffered saline (PBS, 20 mM, pH 9.0, 4 mL) at 37° C. for 24 h in the dark. The films were thoroughly rinsed with deionized water and then visualized using fluorescence microscope (Leica DM4000M).

EXAMPLE 7

Cell Culture on Surface Engineered Biodegradable Polymer Films

The influence of surface chemistry on cell adhesion and growth was studied using P(CL-co-VSC) 8.7% films. The films were prepared and modified with varying thiol-containing molecules including PEG-SH, GC-SH, and GRGDC as above described. The parent unmodified and modified films were placed into a 6-well tissue culture plate and sterilized by radiation prior to use. MG63 osteoblasts were cultured on the films using Dulbecco's modified Eagle medium (DMEM), containing 10% FBS at a density of $1 \times 10^4$ cells/well in a humidified 5% CO$_2$ atmosphere at 37° C. The culture media was set as 4 mL per well and replaced each day. After 1, 4 and 6 d culture, the cells were observed on an inverted fluorescence microscope (Axiovert 40 CFL Microscope equipped with an AxioCam MR3 camera cable), see FIG. 6.

EXAMPLE 8

Synthesis of P(CL-AC-VSC) Copolymer

The ring-opening polymerization was carried out in toluene at 110° C. using ethylene glycol as an initiator and Sn(Oct)$_2$ as a catalyst (Scheme 3). In the P(CL-AC-VSC) copolymer shown in Scheme 3 are x, y, and z molar fractions. The following is a typical example on synthesis of P(CL-AC-VSC) copolymer. In a glovebox under a nitrogen atmosphere, to a stirred solution of ε-CL (3.7 g, 32.45 mmol), AC (0.1 g, 0.5 mmol) and VSC (0.2 g, 0.7 mmol) in toluene (20 mL), ethylene glycol (6.2 mg) and Sn(Oct)$_2$ (48 mg) in their stock solutions were quickly added. The reaction vessel was sealed and placed in an oil-bath thermostated at 110° C. After 48 h polymerization, the reaction was terminated by two drops of acetic acid. A sample was taken for the determination of the monomer conversion using $^1$H NMR. The resulting polymer was isolated by precipitation in cold diethyl ether and dried in vacuo at room temperature. $^1$H NMR showed that the resulting copolymer had degrees of polymerization (DP) of 332, 4 and 6 for CL, AC and VSC, respectively. The copolymer was denoted as P(CL$_{332}$-AC$_4$-VSC$_6$). The compositions could be controlled by the feeding ratio of comonomers (Table 3).

Scheme 3. Ring-opening copolymerization of CL, AC and VSC monomers.

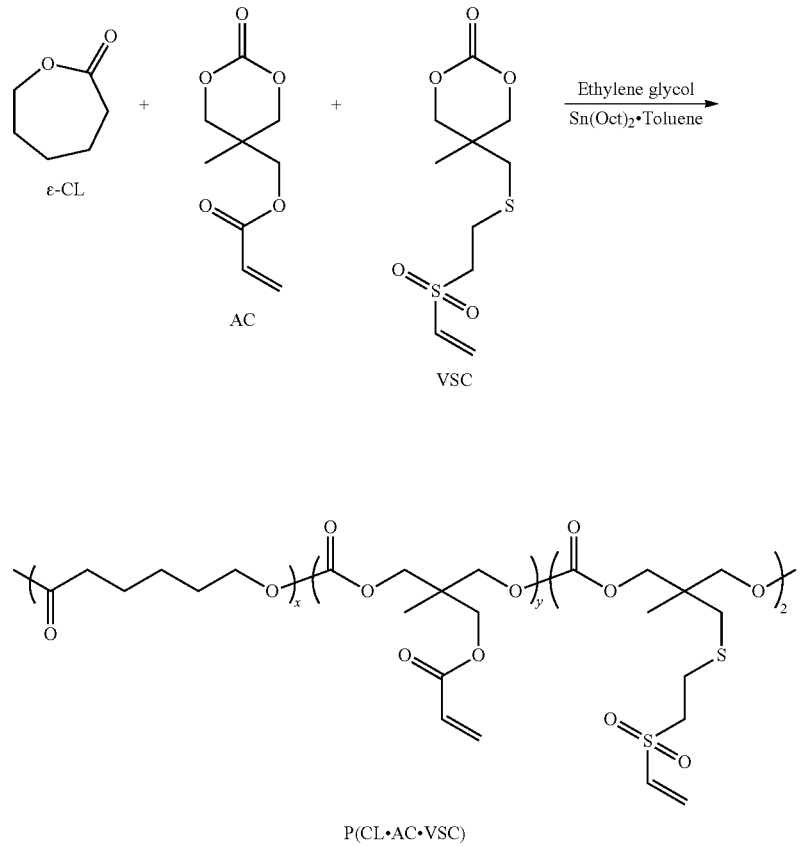

TABLE 3

Synthesis of biodegradable P(CL-AC-VSC) copolymers.[a]

| | | | $M_n \times 10^{-3}$ | | | PDI | |
|---|---|---|---|---|---|---|---|
| Polymer | f[b] | F[c] | theor.[d] | $^1$H NMR[e] | GPC[f] | GPC | Yield |
| P(CL$_{332}$-AC$_4$-VSC$_6$) | 92.5/2.5/5 | 93.8/2/4.2 | 40.0 | 40.3 | 18.0 | 1.9 | 85% |
| P(CL$_{315}$-AC$_{7.8}$-VSC$_3$) | 92.5/5/2.5 | 93.5/4.3/2.2 | 39.4 | 38.3 | 15.4 | 2.3 | 82% |
| P(CL$_{306}$-AC$_{7.5}$-VSC$_{6.5}$) | 90/5/5 | 91.3/4/4.8 | 39.2 | 38.2 | 15.3 | 2.4 | 86% |

[a]The copolymerization was carried out in toluene at 110° C. using ethylene glycol as an initiator and Sn(Oct)$_2$ as the catalyst;
[b]Weight ratio of CL/AC/VSC monomers in feed;
[c]Weight fraction of CL/VSC/AC units determined by $^1$H NMR;
[d]Theoretical molecular weights were calculated based on monomer conversions and monomer-to-initiator ratio;
[f]Estimated by $^1$H NMR end-group analysis;
[g]Determined by GPC (eluent: THF, flow rate: 1.0 mL/min, standards: polystyrene).

EXAMPLE 9

Preparation and Modification of Films

Thin films were prepared on the coverslips using 1.0 wt. % of polymer solution containing 0.02 wt. % I2959 photo-initiator in chloroform. The dried films were crosslinked by photo-irradiation for 10 s ($\lambda$=302 nm). Herein, the P(CL-VSC) copolymer was also taken as a control to confirm that the UV exposure had no effect on the VSC units.

The P(CL-VSC) coating film after UV exposure was characterized by $^1$H NMR, it was found that the film was still dissolved in $CDCl_3$ well and the integral area of double bond ($\delta$ 6.22)/methyl group ($\delta$ 1.03) peak in VSC units was close to 1:3 from the $^1$H NMR spectrum. The P(CL-AC-VSC) coating film after UV exposure was not dissolved in any organic solvent and the strength of the membrane was obviously improved after crosslinking, while the uncrosslinked film was fractured immediately when it was immersed in water. It should be noticed that the stability of P(CL-AC-VSC) coating membrane was enhanced through crosslinking of the AC units, and further modification could be performed with the remaining VSC units.

The crosslinked films were immersed in water for 12 h and treated with a series of thiol-containing molecules (R-SH: 2-mercaptoethanol, 2-mercaptoethyl amine hydrochloride, L-cysteine and chitosan-thiol) at ca. pH 9 (adjusted with $Na_2CO_3$) at r.t. for 16 h. The concentration of the thiol-containing molecules was set as 5 mg/mL. The resulting modified films were rinsed with deionized water for several times and dried over phosphorus pentoxide at r.t. The static contact angle measurements demonstrated that the coating films modified with 2-mercaptoethanol, cysteamine, cysteine and glycol chitosan, all displayed increased hydrophilicity as compared to the parent coatings (FIG. 7). Furthermore, the contact angles of the modified coating films with 6.5% molar ratio of VSC units were lower as compared to those of the corresponding coating films containing a 3% molar ratio of VSC units.

EXAMPLE 10

Synthesis of Methyl Vinyl Sulfone PEG Carbonate Monomer

VS-PEG cyclic carbonate monomer was also synthesized in four steps (Scheme 4). To a stirred solution of 3-methyl-3-oxetanemethanol (10.2 g, 0.1 mol) in THF (100 mL) was dropwise added HBr (40%, 40 mL). The reaction mixture was allowed to warm to 25° C. and stirred for 5 h. The reaction mixture was then diluted with $H_2O$ (150 mL) and extracted with diethyl ether (4×150 mL). The organic phase was dried over anhydrous $MgSO_4$ and concentrated to give the desired product (bromo-diol) as a white solid (16.38 g, 90%).

To a stirred solution of bromo-diol (16.38 g, 0.09 mol) in DMF (150 mL) was added NaSH (22.23 g, 0.27 mol). The reaction mixture was stirred at 75° C. for 17 h, cooled to 25° C., diluted with ultrapure water (1 L), and extracted with EtOAc (3×250 mL). The organic phase was dried over anhydrous $MgSO_4$ and concentrated. Residual DMF was removed by distillation under reduced pressure to give mercapto-diol as viscous yellowish oil (50.26 g, 43%).

To a stirred solution of PEG divinyl sulfone (8.8 g, 26.8 mmol) in MeOH (200 mL) under stirring was dropwise added mercapto-diol (1.0 g, 6.7 mmol) in MeOH. The reaction mixture was allowed to warm to 30° C. and stirred for 2 days in the dark. The solution was concentrated under reduced pressure and the residue was purified by column chromatography (eluent: MeOH/dichloromethane=1/1, v/v) to give the product, VS-PEG-diol (2.0 g, 62%).

To a stirred solution of PEG vinyl sulfone-diol (2.0 g, 4.2 mmol) and ethyl chloroformate (0.9 mL, 8.8 mmol) in dry THF (100 mL) at 0° C. was dropwise added $Et_3N$ (1.4 mL, 10.0 mmol) dissolved in THF. The reaction was allowed to proceed for 8 h at 0° C. The reaction mixture was filtered and the filtrate was concentrated under reduced pressure The crude product was purified by column chromatography (eluent: MeOH/dichloromethane=1/1, v/v) to yield VS-PEG carbonate monomer (1.05 g, 50%).

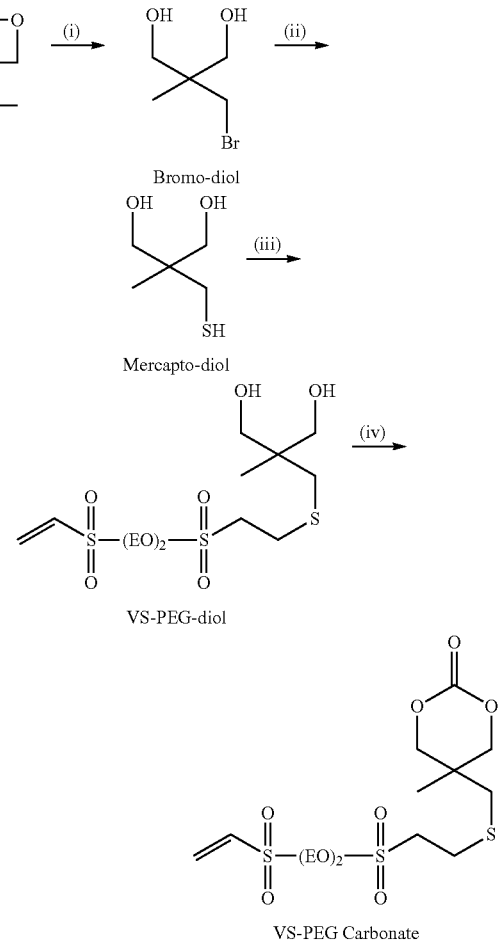

Scheme 4. Synthetic pathway for VS-PEG carbonate monomer.

Conditions: (i) 40% hydrobromic acid, 0° C., 5 h, THF; (ii) sodium hydrosulphide, 75° C., 17 h, DMF; (iii) PEG divinyl sulfone, 30° C., methanol; (iv) ethyl chloroformate, $Et_3N$, 0° C., 4 h, THF.

In conclusion, it has been demonstrated that vinyl sulfone-functionalized biodegradable polymers provide an unprecedented and robust access to advanced functional biomaterials as well as coatings. This represents an efficient and clean (without catalyst and by-products) modification of biodegradable coatings under aqueous conditions. These vinyl sulfone-functionalized biodegradable polymers open a brand-new avenue to engineering the surface chemistry of biomedical devices and coatings and these vinyl sulfone-

EXAMPLE 11

Synthesis of VS-PEG Functionalized Copolymer

The ring-opening copolymerization of VS-PEG carbonate was carried out similar to Example 3. In a glovebox under a nitrogen atmosphere, to a stirred solution of ε-CL (0.218 g, 1.8 mmol) and VS-PEG carbonate (0.1 g, 0.2 mmol) in toluene (4 mL) under stirring were quickly added the stock solutions of isopropanol (1.2 mg, 0.02 mmol) and $Sn(Oct)_2$ (9.3 mg, 0.02 mmol) in toluene. The reaction vessel was sealed and placed in an oil-bath thermostated at 110° C. After 48 h polymerization, the reaction was terminated by one drop of acetic acid. The resulting polymer was isolated by precipitation in cold diethyl ether and dried in vacuo at room temperature. Yield: 0.271 g (85.2%).

The invention claimed is:

1. Method for making a polymer wherein during ring opening polymerisation is incorporated into the polymer chain at least one cyclic (alkyl) carbonate monomer having the formula (1)

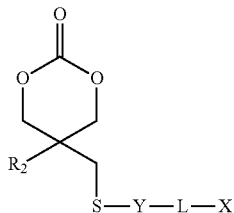

(1)

wherein Y is optional and represents the residue of a sulfhydryl reacted group, X represents a functional group reactive with a sulfhydryl group, L=—[CH2]n with n=0-10, or L=—[CH2]p-S—S—[CH2]q with p and q are 0-5 or L=-[PEG]- with PEG is a group that comprises a —[CH2CH2O]m- group with m=1-200, and R2 is hydrogen, methyl or ethyl.

2. Method as claimed in claim 1, wherein at least one monomer is a cyclic (alkyl) vinyl sulfone carbonate having formula (2)

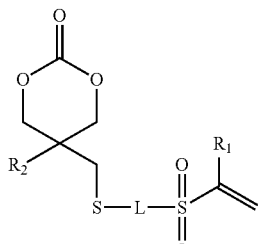

(2)

wherein $R_1$ is hydrogen, $R_2$ has the above identified meaning, and L represents a —$CH_2CH_2$— group, or a —$CH_2CH_2SO_2$-PEG-group, wherein PEG represents an agent comprising at least one —$[CH_2CH_2O]_n$— group, wherein n is 1-200.

3. Method as claimed in claim 1, wherein one monomer is a pegylated cyclic (alkyl) carbonate having the formula (3)

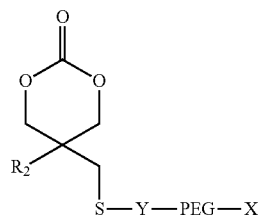

(3)

wherein Y represents the residue of a sulfhydryl reacted group, X represents a functional group reactive with sulfhydryl group, and $R_2$ and PEG have the above identified meaning.

4. Method as claimed in claim 1, wherein the cyclic (alkyl) carbonate monomer is independently selected from the group comprising
   i. the monomer of formula (1A)

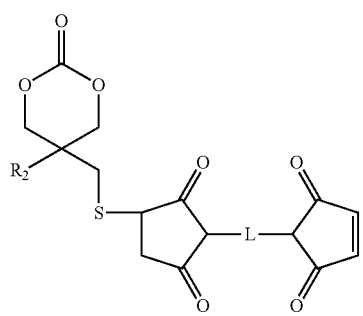

(1A)

ii. the monomer of formula (1B)

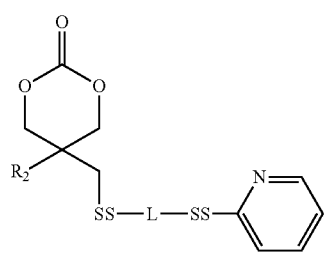

(1B)

iii. the monomer of formula (1C)

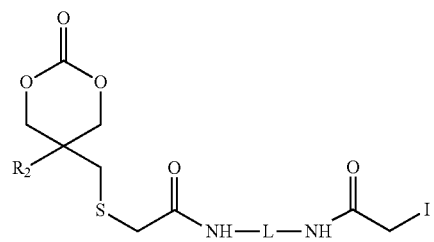

(1C)

iv. vii the monomer of formula (1 D)

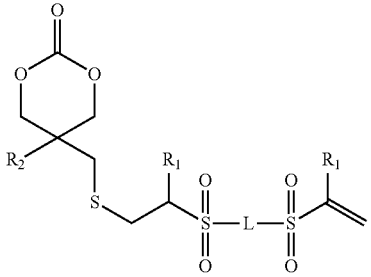
(1D)

wherein $R_1$ is hydrogen, methyl or ethyl and $R_2$ and L have the above identified meaning, and preferably L represents PEG.

5. Method according to claim 1, wherein the polymer is an (alkyl) polycarbonate or copolycarbonate thereof, comprising the steps of:
   i. providing at least one monomer a cyclic (alkyl) carbonate having the formula (1) wherein R2 is hydrogen, methyl or ethyl, and X is a functional group reactive with sulfhydryl group; and
   ii. polymerising by ring opening polymerisation the monomer or monomers thereby making as the polymer the sulfhydryl reactive polycarbonate or copolycarbonate.

6. The method as claimed in claim 5, wherein in step (i) is added a cyclic (alkyl) acryloyl carbonate having the formula (4)

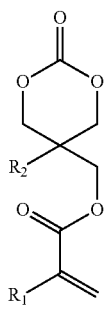
(4)

wherein $R_1$ and $R_2$ each independently are hydrogen, methyl or ethyl thereby forming as the polymer a sulfhydryl reactive, (alkyl) acryloyl copolycarbonate.

7. Method as claimed in claim 1, wherein (an) additional monomer(s) is/are selected from the group comprising
a cyclic $C_3$-$C_{14}$-alkylester having the formula (5)

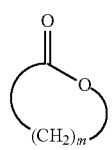
(5)

m=3-14, such as δ-valerolactone, ε-caprolactone and ω-pentadecalactone;
a cyclic diester having the formula (6)

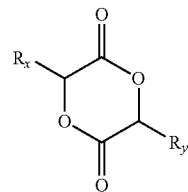
(6)

wherein $R_x$ and $R_y$ each independently are hydrogen, methyl or ethyl, such as lactide;
a morpholinedione having the formula (7)

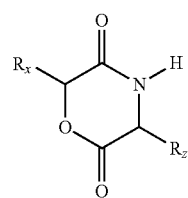
(7)

wherein $R_x$ is hydrogen, methyl or ethyl and independently $R_z$ is hydrogen, methyl, ethyl, or an amino acid residue which is optionally protected;
a dioxanone having the formula (8)

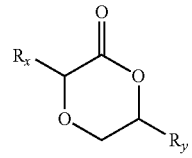
(8)

wherein $R_x$ and $R_y$ each independently are hydrogen, methyl or ethyl; and/or
a cyclic $C_3$-$C_5$-alkylcarbonate having the formula (9)

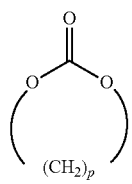
(9)

wherein p=3-5, such as trimethylene carbonate.

8. Method as claimed in claim 1, wherein the polymer is formed into a polymer article, such as a polymer film, such as a (drug eluting) coating.

9. Method as claimed in claim 8, wherein the at least one sulfhydryl reactive group, such as the maleimide group, orthopyridylgroup, iodoacetamide group, (alkyl) vinyl sulfone group and optionally the (alkyl) acryloyl group of the polymer or polymer article, is modified by a functional ligand.

10. Method as claimed in claim 9, wherein the modification comprises a reaction with a thiol-containing functional ligand and/or with an amine-containing functional ligand, and preferably the thiol-containing functional ligand is 2-mercaptoethanol, 3-mercaptopropanoic acid, cysteamine, cysteine, and arginine-glycine-aspartic acid-cysteine (RGDC) peptide, a mercapto saccharide, PEG-SH, H2N-PEG-SH and/or preferably the amine-containing functional ligand is PEG-NH$_2$, or 2-amino ethanol.

11. Method as claimed in claim 9, wherein the modification comprises a reaction with the functional sulfhydryl group reactive group M, such as the vinyl sulfone group, that is carried out in aqueous medium, preferably in the absence of a catalyst.

12. Method as claimed in claim 8, wherein the polymer comprises at least one (alkyl) acryloyl carbonate group, and the polymer and/or the polymer article is cross linked by a photo-crosslinking and/or gamma irradiation of the (alkyl) acryloyl group.

13. Method as claimed in claim 12, wherein the crosslinking comprises crosslinking of other sulfhydryl reactive groups than an (alkyl) acryloyl group by a reaction with a di-thiol, a di-amine, an aminothiol such as 1,6-hexanedithiol, ethylene diamine, 2-mercaptoethylamine, or combinations thereof.

14. Method as claimed in claim 1, wherein the polymerisation is a block copolymerisation comprising at least two polymer blocks, such as of each monomer.

15. Method as claimed in claim 1, wherein the polymerisation is performed with a multifunctional polymerisation initiator having a linear shape, branched shape, or star shape, and preferably the multifunctional polymerisation initiator is a multifunctional PEG.

16. A polymer, (drug eluting) polymer coating or polymer article obtainable by the method according to claim 1, optionally functionalized and/or crosslinked.

17. A biodevice, such as a stent, blood vessel, and cell compartment, comprising or have been made using at least one polymer or polymer article according to claim 16.

18. The biodevice as claimed in claim 17, wherein at least one biologically active agent, such as a drug, a protein, (oligo)-peptide, an aptamer, a nucleic acid such as DNA and RNA, an anti-coagulant, a non-fouling agent, an antibody or an enzyme, and combinations thereof is/are bound to the polymer, directly or indirectly, for instance via a hydrogel-like layer.

19. The polymer according to claim 16, for use in making biodevices, and/or for use in medicine.

20. A cyclic carbonate monomer having:
i. the formula (1)

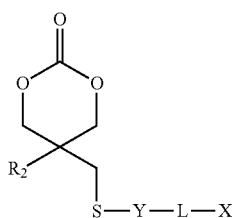

(1)

wherein Y is optional and represents the residue of a sulfhydryl reacted group, X represents a functional group reactive with a sulfhydryl group, L=—[CH2]n with n=0-10, or L=—[CH2]p-S—S—[CH2]q with p and q are 0-5 or L=-[PEG]- with PEG is a group that comprises a —[CH2CH2O]m- group with m=1-200, and R2 is hydrogen, methyl or ethyl;

ii. the formula (2)

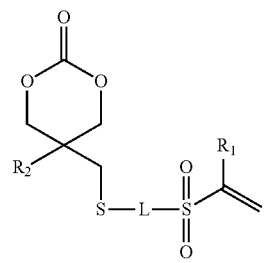

(2)

wherein R1 is hydrogen, R2 has the above identified meaning, and L represents a —CH2CH2- group, or a —CH2CH2SO2-PEG-group, wherein PEG represents an agent comprising at least one —[CH2CH2O]n- group, wherein n is 1-200;

iii. the monomer of formula (1A)

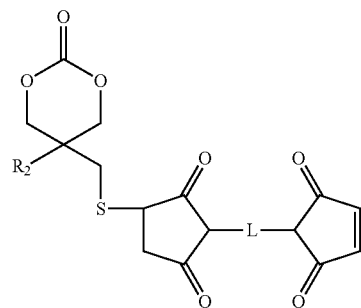

(1A)

iv. the monomer of formula (1B)

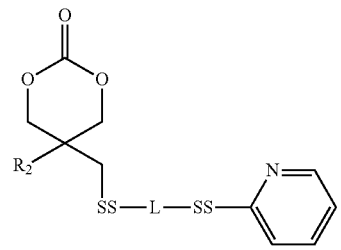

(1B)

v. the monomer of formula (1C)

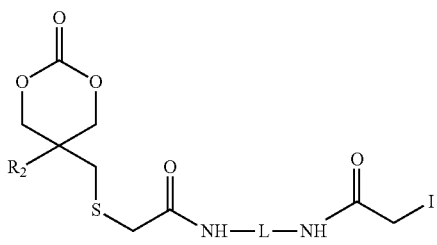
(1C)

vi. vii the monomer of formula (1 D)

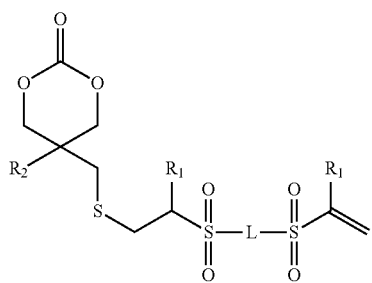
(1D)

wherein $R_1$ is hydrogen, methyl or ethyl and $R_2$ and L have the above identified meaning;

vii. the formula (3)

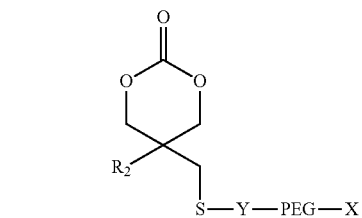
(3)

wherein Y represents a sulfhydryl reactive group, X represents a functional group reactive with sulfhydryl group, and $R_2$ and PEG have the above identified meaning, and preferably of formula (3A)

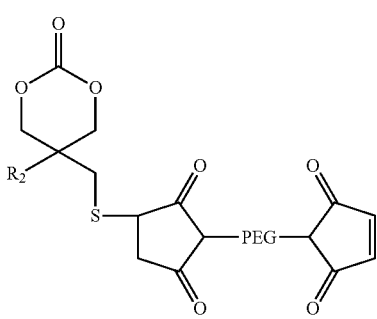
(3A)

or formula (3B)

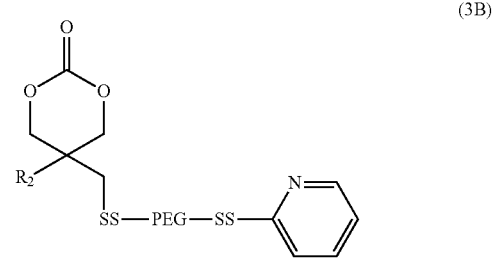
(3B)

and/or of formula (3C)

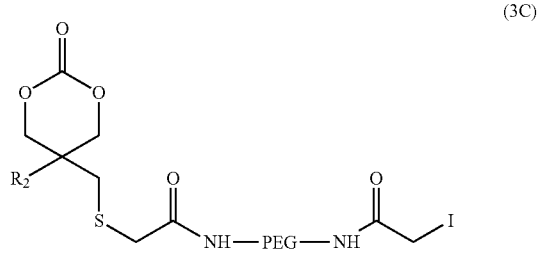
(3C)

wherein R2 and PEG have the above identified meaning, viii. the formula (2A) and/or the formula (2B):

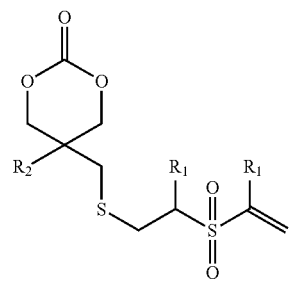
(2A)

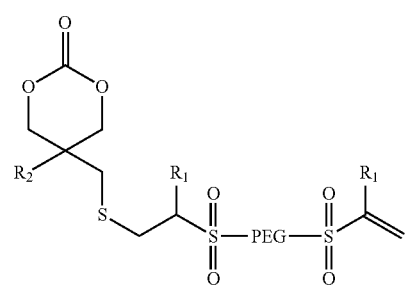
(2B)

wherein R1, R2, and PEG have the above identified meaning.

\* \* \* \* \*